(12) United States Patent
Kato

(10) Patent No.: US 9,335,312 B2
(45) Date of Patent: May 10, 2016

(54) METHOD FOR ASSEMBLING GAS SENSOR, AND GAS SENSOR ASSEMBLY APPARATUS

(71) Applicant: NGK INSULATORS, LTD., Nagoya-shi, Aichi (JP)

(72) Inventor: Kenji Kato, Handa (JP)

(73) Assignee: NGK INSULATORS, LTD., Nagoya (JP)

(*) Notice: Subject to any disclaimer, the term of this patent is extended or adjusted under 35 U.S.C. 154(b) by 326 days.

(21) Appl. No.: 14/139,366

(22) Filed: Dec. 23, 2013

(65) Prior Publication Data
US 2014/0102170 A1   Apr. 17, 2014

Related U.S. Application Data

(63) Continuation of application No. PCT/JP2012/063169, filed on May 23, 2012.

(30) Foreign Application Priority Data

Jul. 4, 2011  (JP) ................................. 2011-148518

(51) Int. Cl.
*B21D 39/00*  (2006.01)
*G01N 27/407*  (2006.01)
(Continued)

(52) U.S. Cl.
CPC .......... *G01N 33/0009* (2013.01); *G01M 15/102* (2013.01); *G01N 27/4078* (2013.01); *Y10T 29/49826* (2015.01)

(58) Field of Classification Search
CPC .......... G01N 27/4078; G01N 33/0009; G01M 15/102; Y10T 29/49826
See application file for complete search history.

(56) References Cited

U.S. PATENT DOCUMENTS

| 4,732,663 A | 3/1988 | Kato et al. |
| 5,948,963 A | 9/1999 | Kato et al. |

(Continued)

FOREIGN PATENT DOCUMENTS

| EP | 0880025 A1 | 11/1998 |
| JP | 10-318980 A | 12/1998 |

(Continued)

OTHER PUBLICATIONS

The International Search Report for the corresponding International Patent Application No. PCT/JP2012/063169 issued on Jun. 29, 2012.

(Continued)

*Primary Examiner* — Lisa Caputo
*Assistant Examiner* — Punam Roy
(74) *Attorney, Agent, or Firm* — Global IP Counselors, LLP

(57) ABSTRACT

Provided are a method of reliably assembling a gas sensor. A plurality of annular mounting members are repeatedly subjected to following steps: bringing a sensor element into an upper-side held state in which the element is held such that an upper end thereof extends vertically with a lower end thereof being inserted into a recess; fitting a through hole of an annular mounting member with the upper end of the element brought in to the upper-side clamped state; and switching from the upper-side held state to a lower-side held state in which the element is held such that the lower end thereof extends vertically, to thereby cause the annular mounting member to reach a predetermined annularly mounting position. Then, the resultant intermediate assembly product is sandwiched by a centering device to minimize the outside diameter thereof, and thereafter, a tubular body is annularly mounted to the intermediate assembly product.

8 Claims, 22 Drawing Sheets

(51) Int. Cl.
*G01N 33/00* (2006.01)
*G01M 15/10* (2006.01)

(56) References Cited

U.S. PATENT DOCUMENTS

| | | | |
|---|---|---|---|
| 6,311,543 B1 * | 11/2001 | Yoshikawa | G01N 27/4071 73/23.2 |
| 7,569,792 B2 * | 8/2009 | Yamada | G01N 27/4062 219/121.63 |
| 2006/0162422 A1 | 7/2006 | Geier et al. | |
| 2015/0253298 A1 * | 9/2015 | Isaka | G01N 33/0009 29/592.1 |
| 2015/0260697 A1 * | 9/2015 | Isaka | G01N 33/0009 29/428 |
| 2015/0268187 A1 * | 9/2015 | Adachi | G01N 27/4078 204/424 |

FOREIGN PATENT DOCUMENTS

| | | |
|---|---|---|
| JP | 2000-111511 A | 4/2000 |
| JP | 2008-145339 A | 6/2008 |
| JP | 2010-237043 A | 10/2010 |
| JP | 2010-266361 A | 11/2010 |

OTHER PUBLICATIONS

The Written Opinion of the International Searching Authority for the corresponding International Patent Application No. PCT/JP2012/063169 issued on Jun. 29, 2012.

Extended European Search Report for the corresponding European patent application No. 12807251.9 issued on Jan. 8, 2015.

\* cited by examiner

F I G. 1
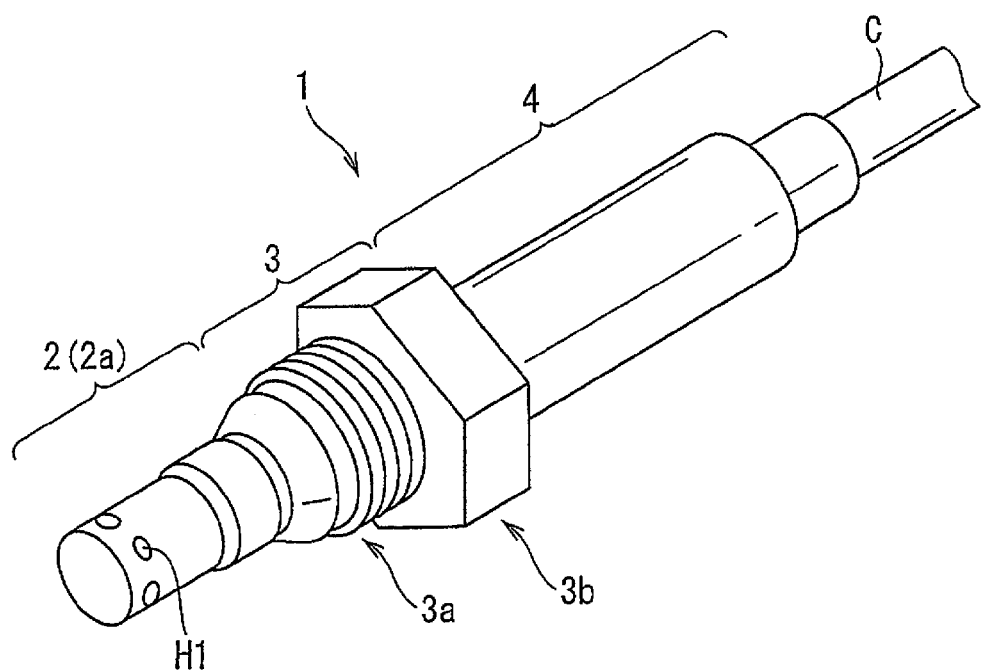

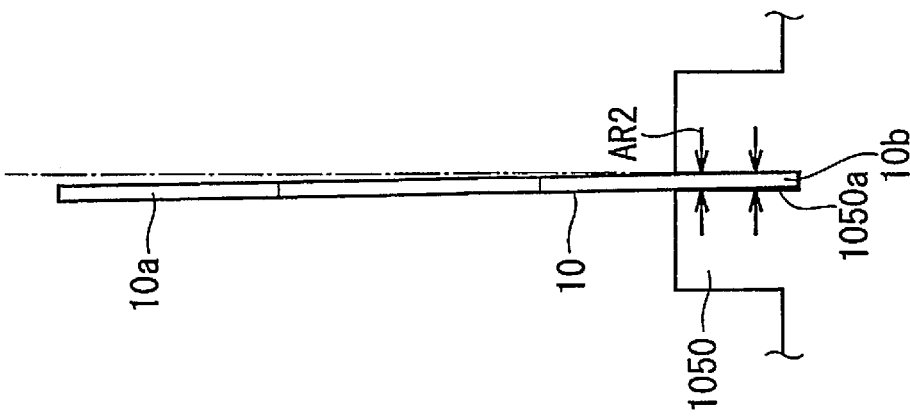
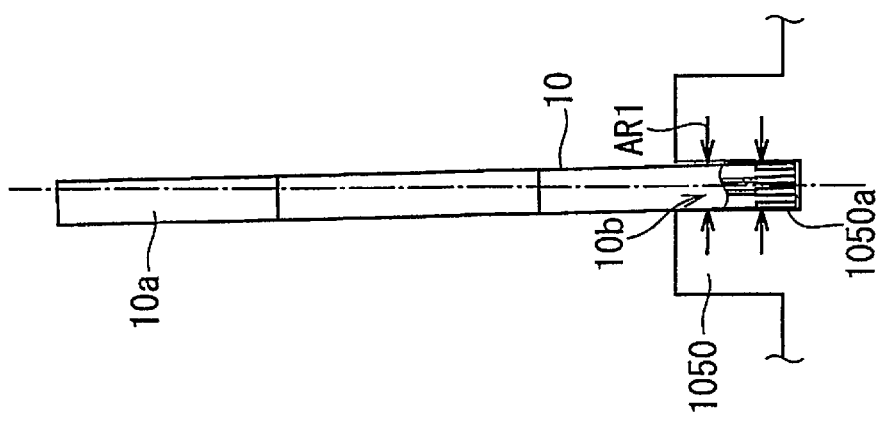

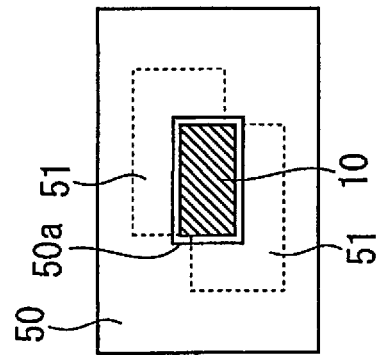
F I G. 8B
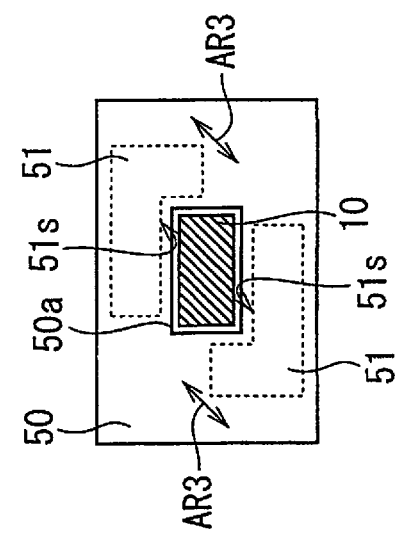
F I G. 8A

F I G. 1 1
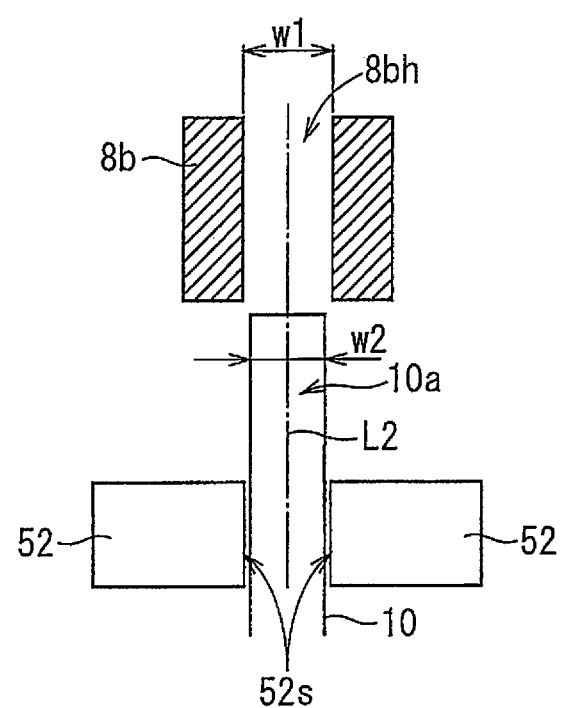

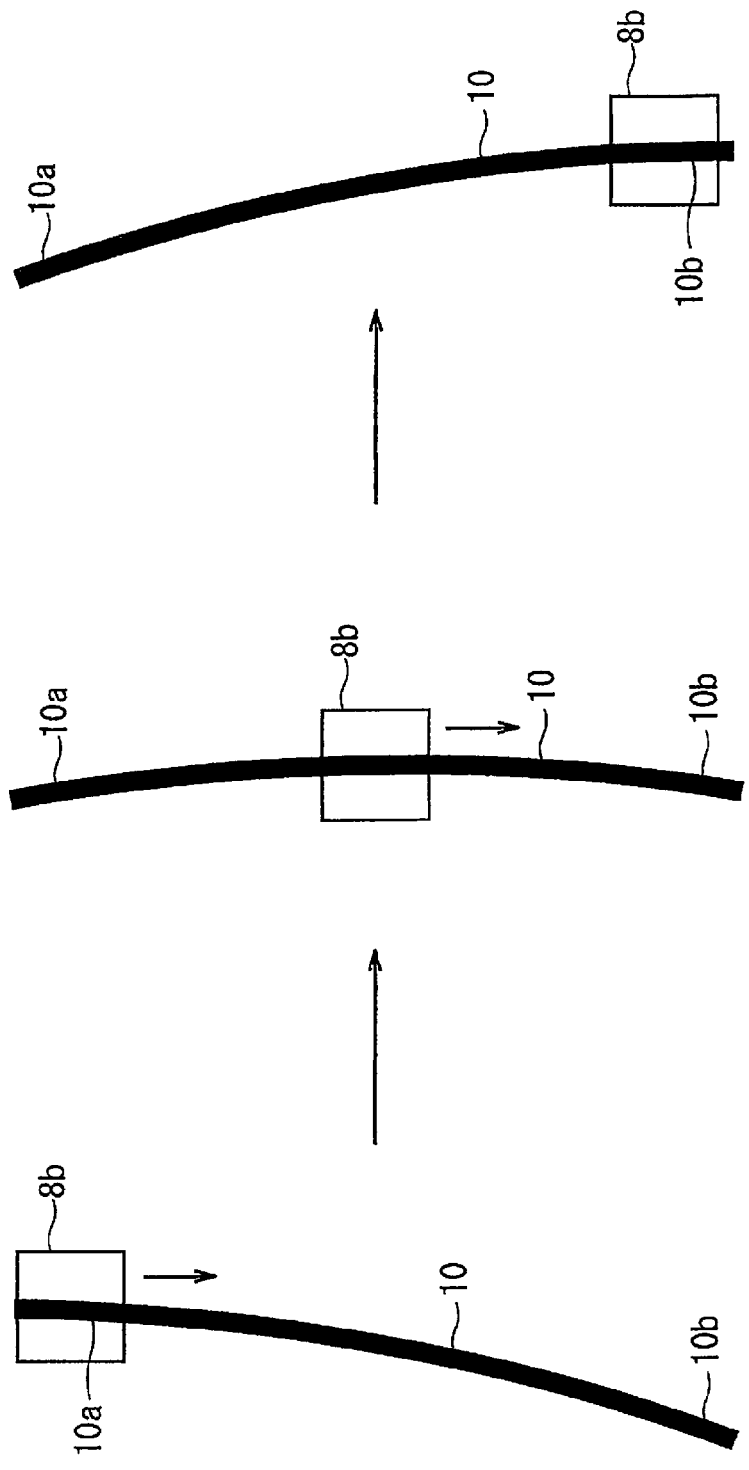

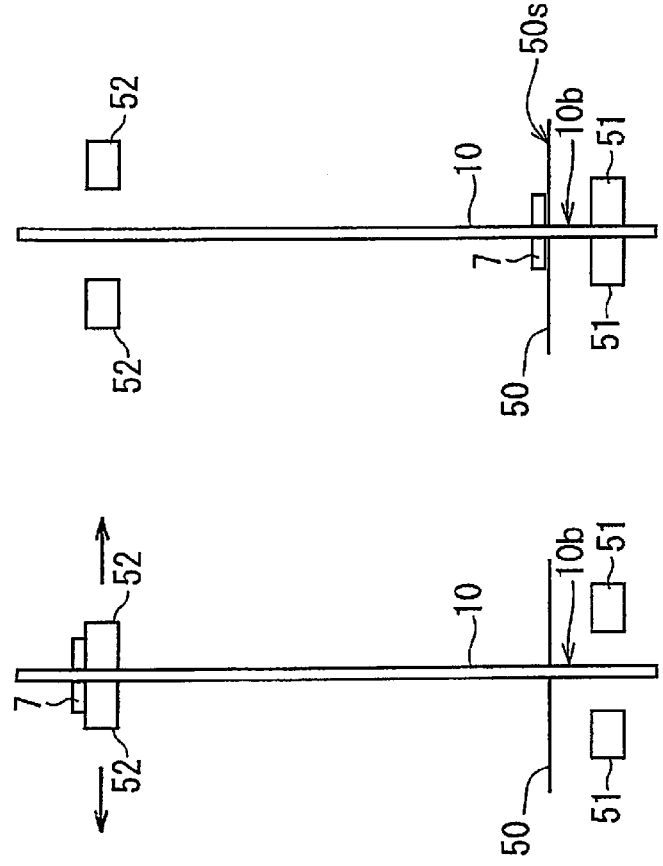

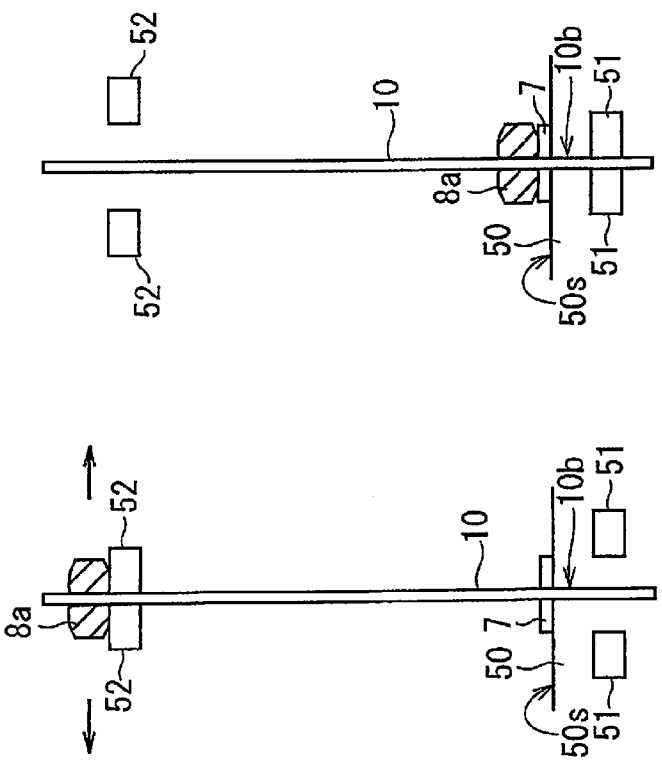

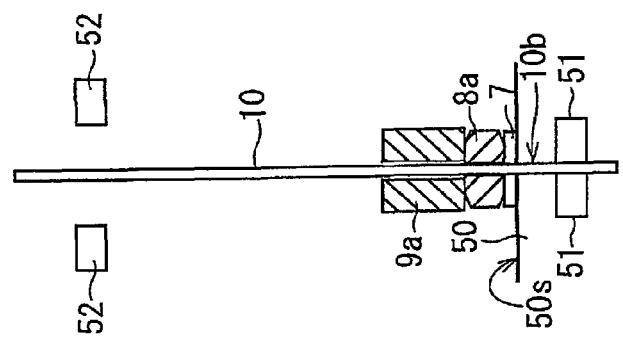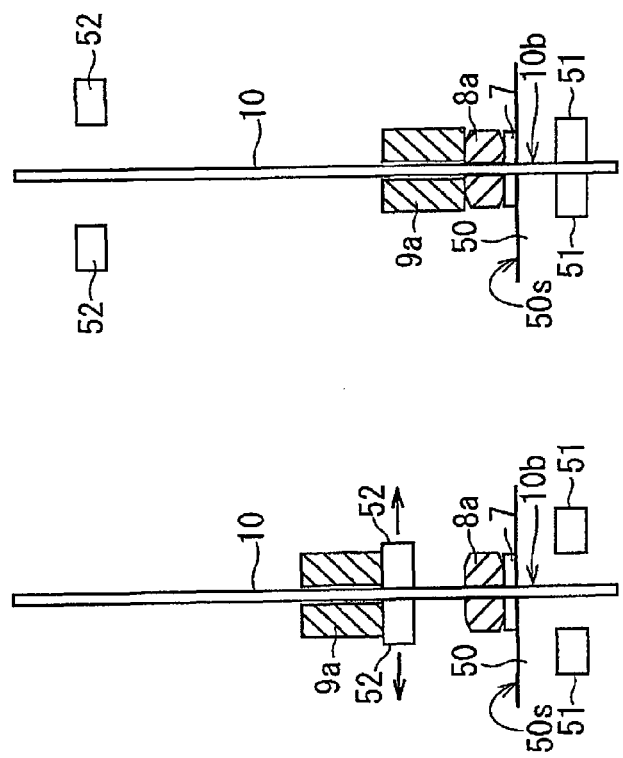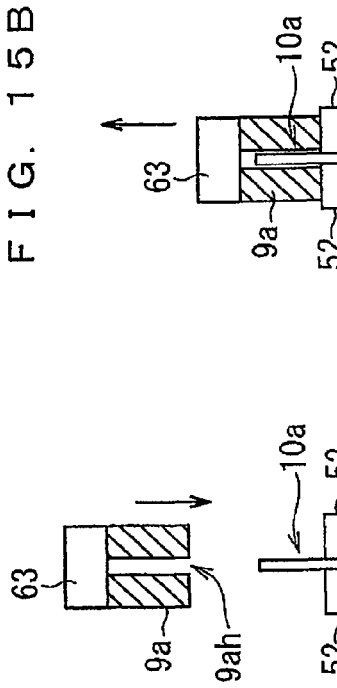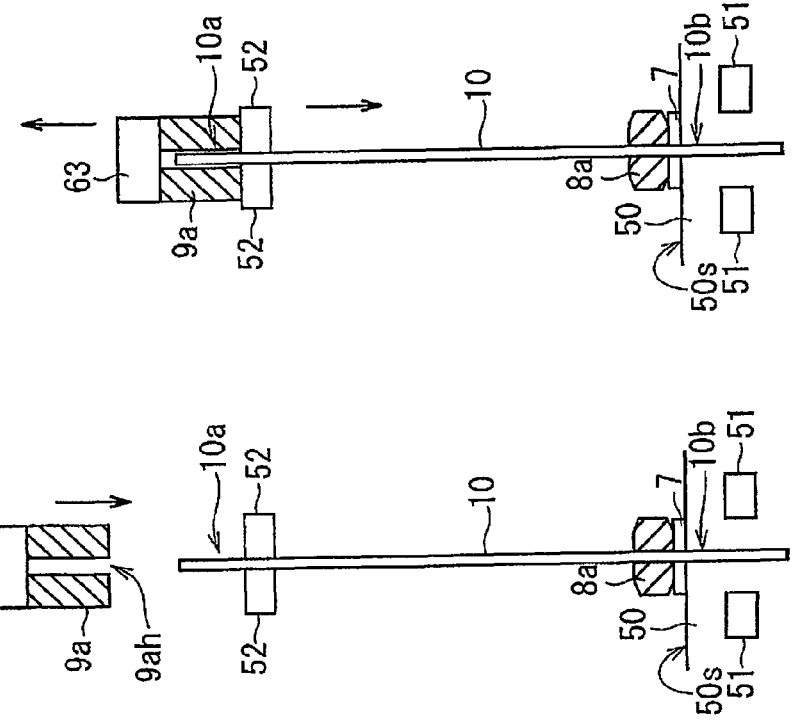

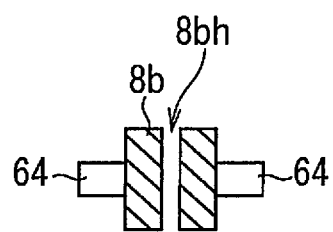
FIG. 16A
FIG. 16B
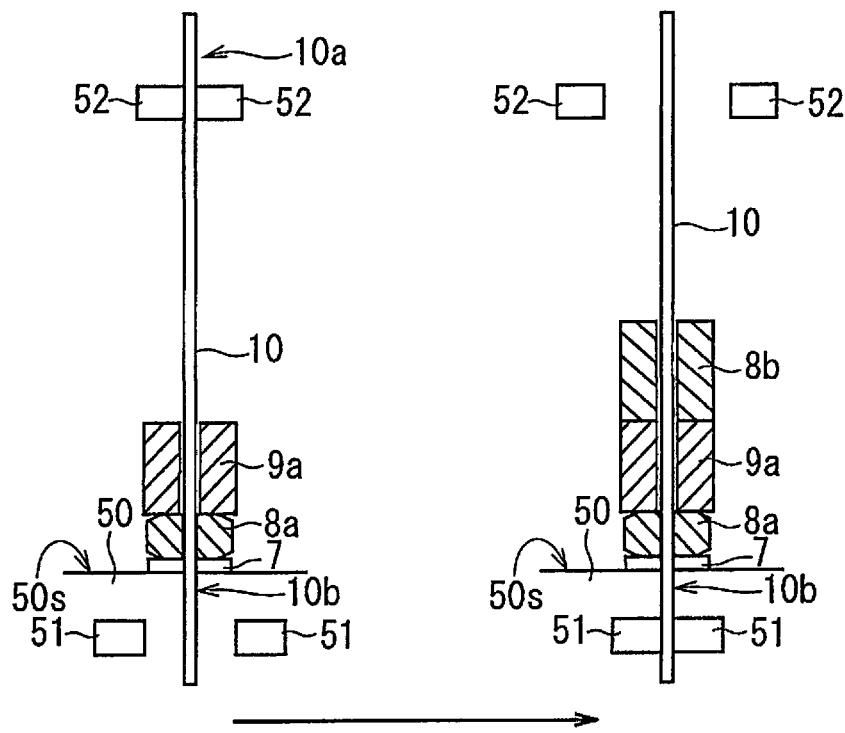

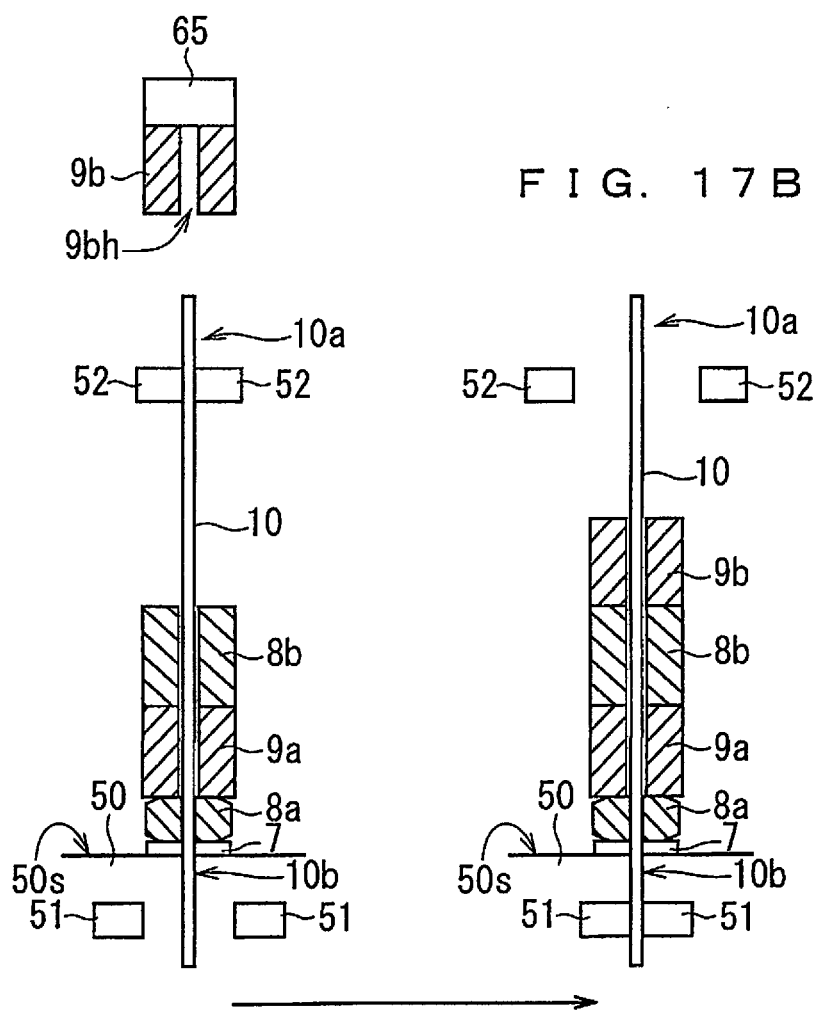

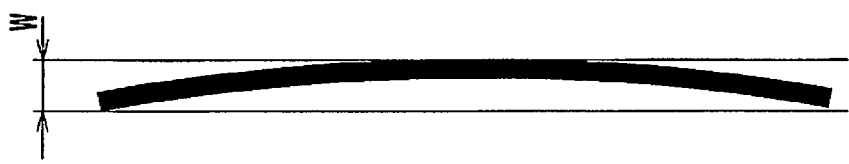
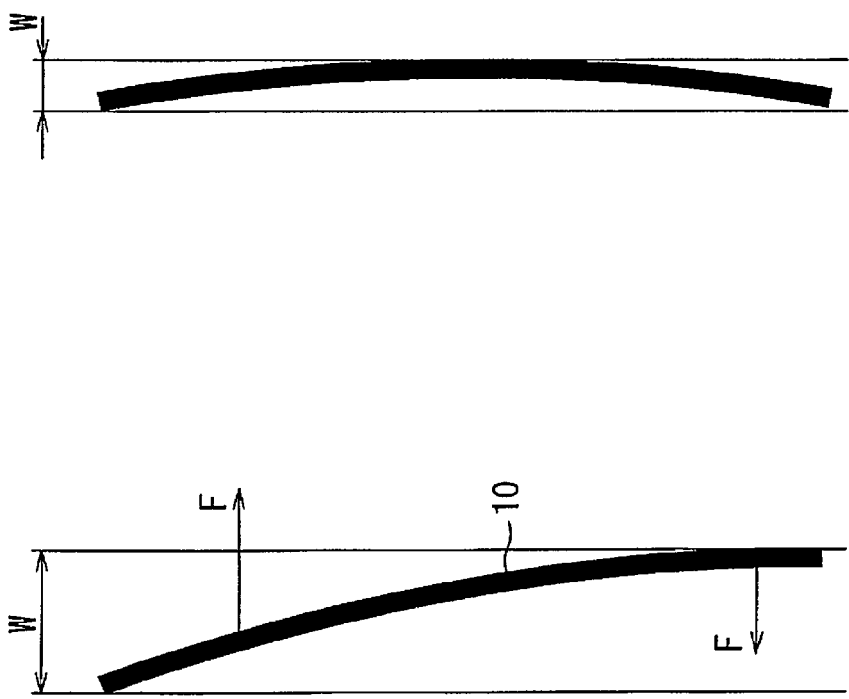

METHOD FOR ASSEMBLING GAS SENSOR, AND GAS SENSOR ASSEMBLY APPARATUS

TECHNICAL FIELD

The present invention relates to a method for assembling a gas sensor including a ceramic sensor element and to an assembly apparatus for use in assembling the same.

BACKGROUND ART

The NOx sensor including a sensor element formed of an oxygen-ion conductive solid electrolyte ceramic such as zirconia ($ZrO_2$) has been conventionally known as a device for measuring a NOx concentration in a measurement gas such as an exhaust gas and a combustion gas in an internal combustion engine, usually a car engine (for example, see Patent Document 1). Such a NOx sensor obtains the concentration of the NOx gas by utilizing a fact that upon decomposition of the NOx gas at a measuring electrode, the amount oxygen ions generated at that time is proportional to the amount of a current (also referred to as a NOx signal) flowing through the measuring electrode and a reference electrode.

In the gas sensor according to Patent Document 1, a ceramic sensor element is fixed by a plurality of ceramic supporters made of ceramic insulator and ceramic powder compacts each filled between the ceramic supporters, such as talc, in a metallic housing and a hollow portion of a cylindrical inner tube welded and fixed to the housing, and is hermetically sealed with the powder compacts.

The step of assembling a gas sensor disclosed in Patent Document 1 includes the step of sequentially fitting through holes, which are provided at the axis center positions of the ceramic supporters and powder compacts, with the sensor element to annularly mount the members to the sensor element, and the step of fitting the intermediate assembly product, which is obtained by annularly mounting the ceramic supporters and powder compacts to the sensor element, with the cylindrical inner tube to annularly mounting the inner tube to the intermediate assembly product.

In the fitting step as described above, if a part serving as an axis warps and a clearance between fitting portions of the respective parts is narrow, the part serving as an axis may interfere with the fitting parts, which does not allow the parts to be fitted in a predetermined manner.

For the gas sensor as disclosed in Patent Document 1, the airtightness between the measurement gas space and reference gas space needs to be secured for preventing the measurement gas from flowing into the reference gas space, while the size of the gas sensor is desired to be minimized because it is provided in an exhaust pipe of the internal combustion engine of, for example, a car. This requires to reduce the inside diameter of the inner tube as well as the sizes of the ceramic supporters and powder compacts and to set a dimensional tolerance smaller than that of a typical fitting part. In other words, the assembly to be made in a situation in which a sufficient clearance is not secured is required. This may result in a case where the ceramic supporter or powder compact interferes with the sensor element or the intermediate assembly product interferes with the inner tube, hindering smooth assembly. In particular, such an interference tends to occur in automation of the above-mentioned assembly step. Also, even in a case where a sensor element whose warping poses no problem in element characteristics is used in assembly, the assembly may be made poorly due to the above-mentioned interference that has occurred.

Setting of a dimension and tolerance for sufficiently securing a clearance between fitting parts may reduce such problems, which is not desirably employed from viewpoints of hermitic sealing and size reduction of an element as described above.

PRIOR ART DOCUMENT

Patent Document

Patent Document 1: Japanese Patent Application Laid-Open No. 10-318980 (1998)

SUMMARY OF INVENTION

The present invention has been made in view of the above-mentioned problems, and an object thereof is to provide an assembly method capable of assembling a gas sensor more reliably than before and an assembly apparatus capable of performing the assembly method even in a case where a sensor element warps.

In order to solve the above-mentioned problems, a first aspect of the present invention relates to a method for assembling a gas sensor, where: a lower-side held state denotes a state in which a predetermined position on a lower end side of a sensor element is sandwiched by first sandwich means with the lower end being inserted into a recess of a predetermined holder, to thereby hold the sensor element such that at least the lower end extends vertically, the sensor element including ceramic as a main constituent material and having an elongated shape; and an upper-side held state denotes a state in which a predetermined position on an upper end side of the sensor element is sandwiched by second sandwich means with the lower end being inserted into the recess, to thereby hold the sensor element such that at least the upper end extends vertically, the method including: a holding step of bringing the sensor element into the upper-side held state; a fitting step of fitting a through hole of an annular mounting member with the upper end of the sensor element brought into the upper-side held state, the annular mounting member having a disc shape or cylindrical shape and having the through hole corresponding to a cross-sectional shape of the sensor element; and a switching step of switching the held state of the sensor element from the upper-side held state to the lower-side held state after the through hole is fitted with the upper end, to thereby cause the annular mounting member to reach a predetermined annularly mounting position.

In a second aspect of the present invention, in the method for assembling a gas sensor according to the first aspect, the holding step, the fitting step, and the switching step are performed on each of a plurality of types of the annular mounting members to obtain an intermediate assembly product.

In a third aspect of the present invention, in the method for assembling a gas sensor according to the second aspect: the plurality of types of annular mounting members include ceramic supporters made of ceramic glass, and ceramic powder compacts; and the ceramic supporters and the powder compacts are annularly mounted alternately.

In a fourth aspect of the present invention, a method for assembling a gas sensor includes: a first annularly mounting step of obtaining the intermediate assembly product by the method according to the second or third aspect; a centering step of sandwiching the intermediate assembly product from its sides by predetermined centering means in a state where the intermediate assembly product is placed on the holder by inserting the lower end into the recess, thereby minimizing an outside diameter of the intermediate assembly product; and a second annularly mounting step of annularly mounting a tubular body to the intermediate assembly product whose outside diameter has been minimized in the centering step.

In a fifth aspect of the present invention, a gas sensor assembly apparatus includes: a holder having a recess for inserting a sensor element including ceramic as a main constituent material and having an elongated shape; first sandwich means for sandwiching a predetermined position on a lower end side of the sensor element with the lower end of the sensor element being inserted into the recess of the holder; second sandwich means for sandwiching a predetermined position on an upper end side of the sensor element with the lower end of the sensor element being inserted into the recess; an annular mounting member supply portion for supplying an annular mounting member that has a disc shape or cylindrical shape and has a through hole corresponding to a cross-sectional shape of the sensor element; and annular mounting member transport means for transporting the annular mounting member from the annular mounting member supply portion to an annularly mounting process execution position, wherein in a case where: a lower-side held state denotes a state in which a predetermined position on the lower end side of the sensor element is sandwiched by the first sandwich means, to thereby hold the sensor element such that at least the lower end extends vertically; and an upper-side held state denotes a state in which a predetermined position on the upper end side of the sensor element is sandwiched by the second sandwich means, to thereby hold the sensor element such that at least the upper end extends vertically, the held state of the sensor element is switched from the upper-side held state to the lower-side held state after the annular mounting member transport means fits the through hole of the annular mounting member with the upper end of the sensor element brought into the upper-side held state, to thereby cause the annular mounting member to reach a predetermined annularly mounting position.

In a sixth aspect of the present invention, in the gas sensor assembly apparatus according to the fifth aspect, a plurality of the annular mounting member supply portions and a plurality of the annular mounting member transport means are respectively provided correspondingly to a plurality of types of annular mounting members, and an operation is performed for each of the plurality of types of annular mounting members in order, of fitting the through hole of the annular mounting member with the upper end of the sensor element brought into the upper-side held state, by the annular mounting member transport means, and then switching the held state of the sensor element from the upper-side held state to the lower-side held state to cause the annular mounting member to reach a predetermined annularly mounting position, thereby obtaining an intermediate assembly product in which the plurality of types of annular mounting members are annularly mounted to the sensor element.

In an seventh aspect of the present invention, in the gas sensor assembly apparatus according to the sixth aspect: a plurality of the annularly mounting process execution positions are provided correspondingly to the plurality of types of annular mounting members; the gas sensor assembly apparatus further includes holder transport means for transporting the holder between the annularly mounting process execution positions; the holder transport means transports, to the annularly mounting process execution positions, the holder holding the sensor element in order; and an operation is performed at each of the annularly mounting process execution positions, of fitting the through hole of the annular mounting member with the upper end of the sensor element brought into the upper-side held state, by the annular mounting member transport means, and then switching the held state of the sensor element from the upper-side held state to the lower-side held state to cause the annular mounting member to reach a predetermined annularly mounting position, thereby obtaining an intermediate assembly product in which the plurality of types of annular mounting members are annularly mounted to the sensor element.

According to the first to seventh aspects of the present invention, the annular mounting member can be annularly mounted to the sensor element or elongated member with reliability even in a case where the sensor element or elongated member warps and the dimensional tolerance between the annular mounting member and the sensor element or elongated member is small.

According to the fourth aspects of the present invention, the tubular body can be annularly mounted to the intermediate assembly product with reliability even in a case where the sensor element or elongated member warps and the dimensional tolerance between the intermediate assembly product and tubular body is small.

BRIEF DESCRIPTION OF DRAWINGS

FIG. 1 is an external perspective view of a gas sensor 1 to be assembled in an embodiment.

FIGS. 5A and 5B are views showing a state in which a sensor element 10 is held and fixed in conventional first and second assembly steps.

FIGS. 8A and 8B are plan views showing an outline of a holder 50 for use in a first assembly step and a second assembly step in the embodiment.

FIG. 11 is a view showing a state in which a through hole 8$bh$ of a ceramic supporter 8$b$ is fitted with a first tip 10$a$ of the sensor element 10 in an upper-side clamped state.

FIGS. 12A to 12C are conceptual diagrams showing a state during switching of a clamped state.

FIGS. 13A to 13D are views showing a state in which a washer 7 is annularly mounted.

FIGS. 14A to 14D are views showing a state in which a ceramic supporter 8$a$ is annularly mounted.

FIGS. 15A to 15D are views showing a state in which a powder compact 9$a$ is annularly mounted.

FIGS. 16A and 16B are views showing a state in which a ceramic supporter 8$b$ is annularly mounted.

FIGS. 17A and 17B are views showing a state in which a powder compact 9$b$ is annularly mounted.

FIGS. 21A and 21B are diagrams conceptually showing a posture of the sensor element 10 before and after the centering process.

DESCRIPTION OF EMBODIMENTS

Configuration of Gas Sensor

Figure 2:
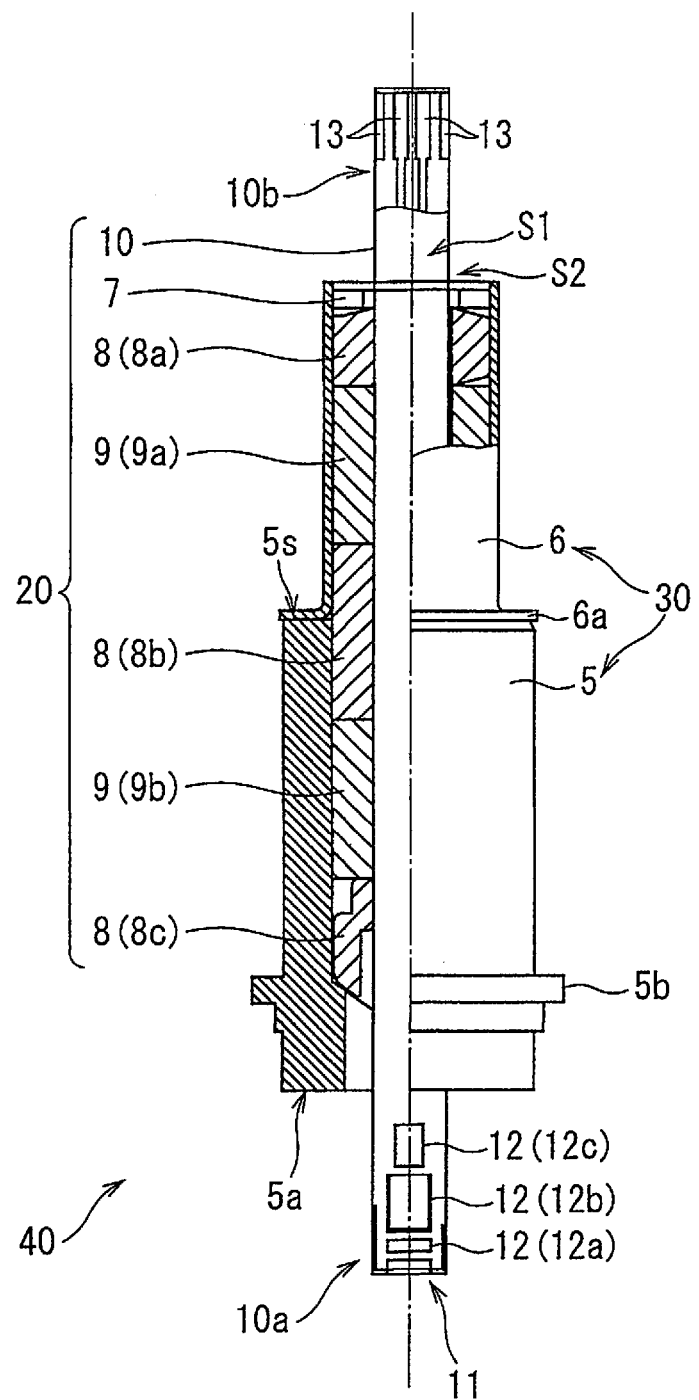
FIG. 2 is a partial cross-sectional view showing a main configuration of an inside of the gas sensor 1.

FIG. 1 is an external perspective view of a gas sensor (more specifically, a main body thereof) 1 to be assembled in this embodiment. FIG. 2 is a partial cross-sectional view showing a main configuration of the inside of the gas sensor 1. In this embodiment, the gas sensor 1 serves to detect a predetermined gas component (such as NOx) with a sensor element 10 (FIG. 2) included therein.

The sensor element 10 is an elongated cylindrical or thin-plate like member including as a main constituent material an element body of oxygen-ion conductive solid electrolyte ceramic such as zirconia. The sensor element 10 has a configuration in which a gas inlet, an internal space, and the like are provided on a first tip 10a side and various electrodes and a wiring pattern are provided on the surface and inside of the element body. In the sensor element 10, a detection gas introduced into the internal space is reduced or decomposed in the internal space, to thereby generate oxygen ions. The gas sensor 1 determines the concentration of the gas component based on a fact that an amount of oxygen ions flowing inside an element is proportional to the concentration of the gas component in a detection gas. In FIG. 2, the surface facing the front surface is referred to as a main surface S1 of the sensor element 10, and the surface that is perpendicular to the main surface S1 and extends along the longitudinal direction is referred to as a side surface S2.

The outside of the gas sensor 1 is mainly formed of a first cover 2, a fixing bolt 3, and a second cover 4.

The first cover 2 is an approximately cylindrical exterior member that protects a portion of the sensor element 10 that comes into direct contact with the detection gas in use, which is specifically the first tip 10a including a gas inlet 11 and a closed space 12 (buffer space 12a, first internal space 12b, and second internal space 12c). For easy understanding, FIG. 2 and the following diagrams show that the gas inlet 11 and the closed space 12 (buffer space 12a, first internal space 12b, and second internal space 12c) are formed in the main surface S1. In actuality, those parts are not exposed in the main surface S1 but are each provided inside the sensor element 10 except for the gas inlet 11 being open at the lowermost end of the sensor element 10 in FIG. 2.

More specifically, the first cover 2 has a double-layer structure of an outside cover 2a and an inside cover (not shown). Each of the outside cover 2a and inside cover has a circular bottom on one side and has a plurality of through holes through which a gas passes in the side portion. FIG. 1 illustrates through holes H1 provided in the outside cover 2a, which are merely an example. The position and number of through holes arranged may be appropriately determined in consideration of how a measurement gas flows into the first cover 2.

The fixing bolt 3 is an annular member to be used when the gas sensor 1 is fixed at a measurement position. The fixing bolt 3 includes a threaded bolt portion 3a and a held portion 3b to be held when the bolt portion 3a is screwed. The bolt portion 3a is screwed with a nut provided at a position at which the gas sensor 1 is mounted. For example, the bolt portion 3a is screwed with a nut portion provided in the car exhaust pipe, whereby the gas sensor 1 is fixed to the exhaust pipe such that the first cover 2 side thereof is exposed in the exhaust pipe.

The second cover 4 is a cylindrical member that protects other part of the gas sensor 1. A cable C for electrically connecting the gas sensor 1 and a drive controller (not shown) extends from the end of the second cover 4.

FIG. 2 shows the internal configuration of the gas sensor 1, more specifically, the configuration of the gas sensor 1 except for the first cover 2, fixing bolt 3, and second cover 4 shown in FIG. 1.

As shown in FIG. 2, inside the gas sensor 1, a washer 7, three ceramic supporters 8 (8a, 8b, and 8c), and two powder compacts 9 (9a and 9b) are each annularly mounted to the part of the sensor element 10 except for the first tip 10a, which includes the gas inlet 11 and the like, and a second tip 10b, which includes terminals 13 for connection with the cable C, such that the sensor element 10 is positioned about the axis. The ceramic supporter 8 is a ceramic insulator. Meanwhile, the powder compact 9 is obtained by shaping ceramic powders such as talc.

Figure 3:
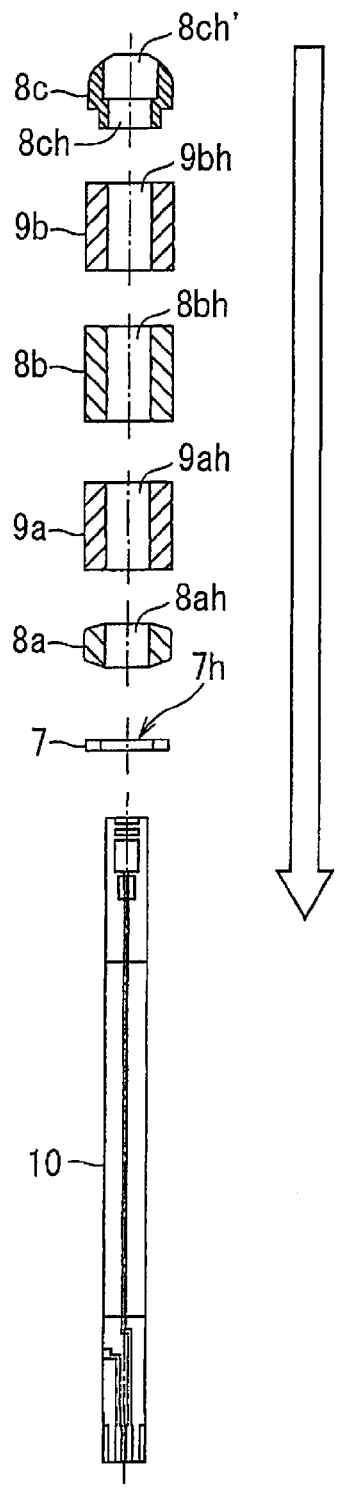
FIG. 3 is a view schematically showing a procedure of assembling an intermediate assembly product 20.

In the following description, the configuration obtained by annularly mounting the washer 7, ceramic supporters 8, and powder compacts 9 to the sensor element 10 is referred to as an intermediate assembly product 20. FIG. 3 is a view schematically showing the procedure of assembling the intermediate assembly product 20.

As shown in FIG. 3, in outline, the intermediate assembly product 20 is assembled by annularly mounting the washer 7, ceramic supporter 8a, powder compact 9a, ceramic supporter 8b, powder compact 9b, and ceramic supporter 8c to the sensor element 10 in this order. Each member has a disc shape or cylindrical shape. For annularly mounting as described above, a circular through hole 7h is provided at the axis center position of the washer 7, and through holes 8ah, 9ah, 8bh, 9bh, and 8ch having a rectangular shape corresponding to the cross-sectional shape of the sensor element 10 are provided in the ceramic supporter 8a, powder compact 9a, ceramic supporter 8b, powder compact 9b, and ceramic supporter 8c, respectively. Those through holes are fitted with the sensor element 10, so that the members are each annularly mounted to the sensor element 10. The part of the ceramic supporter 8c that is opposed to the through hole 8ch is an opening 8ch' open wider than the through hole 8ch. The washer 7, ceramic supporters 8, and powder compacts 9 are coaxially arranged in the intermediate assembly product 20.

From the viewpoint of securing airtightness, the through holes of the ceramic supporters 8 and the through holes of the powder compacts 9 are configured such that a difference with a design cross-sectional size of the sensor element 10 is 0.25 to 0.35 mm and a dimensional tolerance is 0.1 mm. Meanwhile, the through hole 7h of the washer 7 is provided so as to have a difference with the design cross-sectional size of the sensor element 10 of at least 1 mm or more and 1.3 mm or less. The washer 7, ceramic supporters 8, and powder compacts 9 are configured to have a difference in outside diameter value of approximately 0.35 mm at a maximum.

Figure 4:
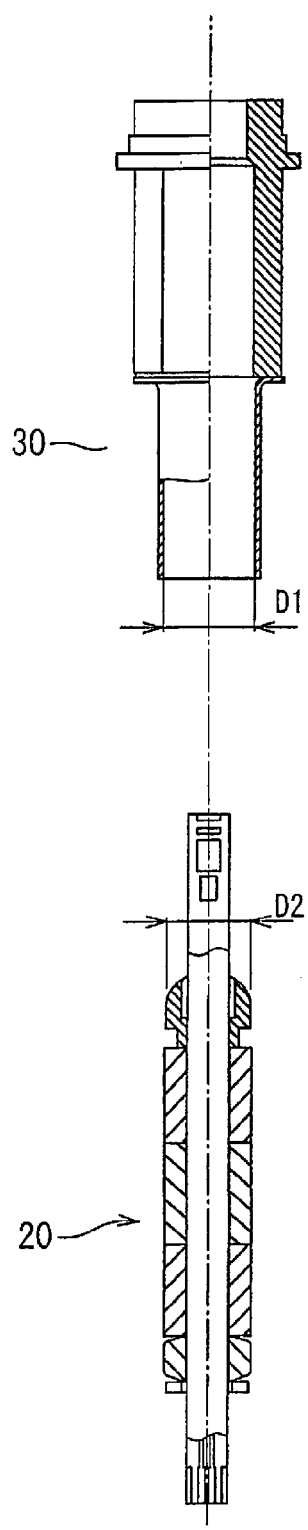
FIG. 4 is a view showing a state in which the intermediate assembly product 20 is fitted into a tubular body 30 to obtain a finished assembly product 40.

As shown in FIG. 2, a cylindrical tubular body (inner tube welded product) 30, which is obtained by integrating a housing 5 being a ceramic cylindrical member and an inner tube 6 being a metallic cylindrical member, is annularly mounted to the intermediate assembly product 20. In the following description, the configuration in which the tubular body 30 is annularly mounted to the intermediate assembly product 20 is referred to as a finished assembly product 40. FIG. 4 shows a state in which the intermediate assembly product 20 is fitted into the tubular body 30 to obtain the finished assembly product 40.

The tubular body 30 is formed by integrally welding a bend 6a bent outwardly, which is included in one end of the inner tube 6, to an end surface 5s of the housing 5. The housing 5 and inner tube 6 have substantially the same inside diameter and are connected coaxially. An inside diameter D1 of the tubular body 30 is set to be larger than a designed value D2 of the maximum outside diameter of the intermediate assembly product 20.

The finished assembly product 40 is obtained by fitting the intermediate assembly product 20 into the tubular body 30 as shown in FIG. 4, and then, an external force is applied in such a direction as to compress the powder compacts 9a and 9b against the intermediate assembly product 20 inside the tubular body 30. As a result, sealing is provided in a region between the first tip 10a of the sensor element 10, which includes the gas inlet 11 and the like, and the second tip 10b thereof, which includes the terminals 13 for connection with the cable C and the like, inside the finished assembly product 40. This secures the airtightness between the measurement gas space and the reference gas space.

The resultant obtained by coating the finished assembly product 40 with the first cover 2, fixing bolt 3, and second cover 4 is the gas sensor 1. Specifically, the first cover 2 is connected to a tubular portion 5a at the tip of the housing 5. The fixing bolt 3 is annularly mounted to the outer periphery of the housing 5 so as to come into contact with a projection 5b. Moreover, the second cover 4 is mounted so as to be fitted into an annular groove between the fixing bolt 3 and housing 5, which is formed through the above annular mounting.

The above-mentioned configuration allows the gas sensor 1 to completely cut off the atmosphere (atmosphere in the first cover 2) around the first tip 10a of the sensor element 10 from the outside atmosphere in a state in which the gas sensor 1 is mounted at a predetermined position. This allows for accurate measurement of the concentration of a target gas component in the detection gas.

<Warp of Sensor Element and Problem with Conventional Assembly Steps>

Although FIGS. 2 to 4 ignore the warp of the sensor element 10 for simplification of the description, in actuality, the sensor element 10 warps slightly, which results from the process of manufacturing the same. Specifically, the slurry as a mixture of ceramic powders and organics is applied onto a predetermined film and then dried, and a plurality of ceramic green sheets cut into a predetermined size are prepared. Then, a predetermined wiring pattern is formed by screen printing or a cavity is formed in each of the ceramic green sheets as required, the green sheets are laminated, and the laminated body is cut and then baked. As a result, the sensor element 10 is manufactured. The shrinkage during the baking causes the sensor element 10 to warp. It is realistically difficult to completely prevent all the sensor elements from warping if various countermeasures are taken to prevent a warp.

An excessive amount of warp affects the characteristics of the sensor element 10, and thus, the sensor element 10 with such a warp is excluded prior to the step of assembling the intermediate assembly product 20 (hereinbelow, this is referred to as a first assembly step). However, the sensor element 10, which does have a warp but it does not exceed a predetermined dimensional tolerance and has no characteristic problems, is usually subjected to the first assembly step. Thus, the assembly needs to be performed in consideration of a warp of the sensor element 10 in the first assembly step and the step of assembling the finished assembly product 40 (hereinbelow, this is referred to as a second assembly step) to be performed subsequently.

FIGS. 5A and 5B, 6A to 6C, and 7A and 7B are views schematically showing the conventional first and second assembly steps. While the descriptions of FIGS. 5A and 5B, 6A to 6C, and 7A and 7B and thereafter are targeted for a case in which the sensor element 10 warps in such a manner that it is curved uniformly in the longitudinal direction and thickness direction thereof, the manner in which the sensor element 10 warps is merely an example, and the direction of the actual warp of the sensor element 10 is not limited to a combination of those directions. Here, the warp of the sensor element 10 is more exaggerated than an actual warp.

FIGS. 5A and 5B show a state in which the sensor element 10 is held and fixed in the conventional first and second assembly steps. FIG. 5A is a view in a case where the sensor element 10 is viewed from the main surface S1 side, while FIG. 5B is a view in a case where the sensor element 10 is viewed from the side surface S2 side in the longitudinal direction.

As shown in FIGS. 5A and 5B, in the conventional technique, the second tip 10b of the sensor element 10 is inserted into a recess 1050a provided vertically downward from the upper surface of a holder 1050, and is then sandwiched by, for example, a clamp mechanism as indicated by arrows AR1 and AR2. As a result, the sensor element 10 is held and fixed in the recess 1050a. This held and fixed state is kept until the second assembly step is finished.

In this case, if the sensor element 10 warps, as shown in FIGS. 5A and 5B, the first tip 10a of the sensor element 10 is positioned to be deviated from the position vertically above the second tip 10b fixed to the holder 1050. In the case shown in FIGS. 5A and 5B, the sensor element 10 is deviated more from the above-mentioned position as more apart from the holder 1050 upwardly.

Figure 6A:
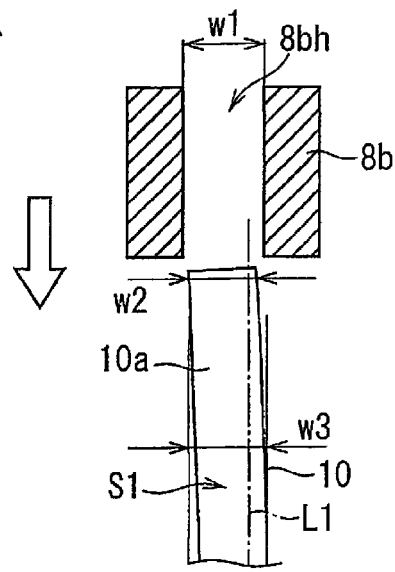
FIGS. 6A to 6C are views showing a state during assembly in the conventional first assembly step.
Figure 6B:
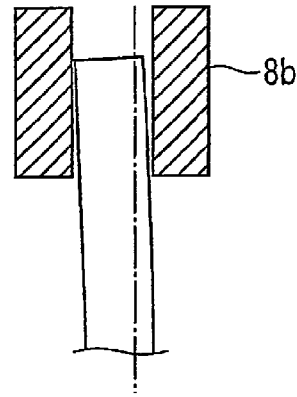
Figure 6C:
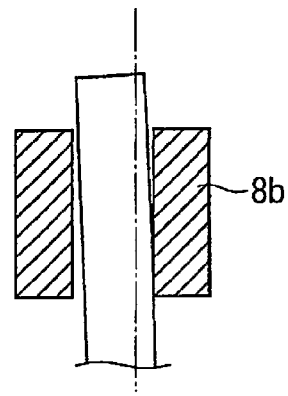

FIGS. 6A to 6C show a state during the assembly of the conventional first assembly step. In the first assembly step, as shown in FIG. 3, the washer 7, ceramic supporter 8a, powder compact 9a, ceramic supporter 8b, powder compact 9b, and ceramic supporter 8c are annularly mounted in this order to the sensor element 10 fixed as shown in FIGS. 5A and 5B from the second tip 10b side, whereby the intermediate assembly product 20 is assembled. FIGS. 6A to 6C illustrates a state in annularly mounting the ceramic supporter 8b of those members from the first tip 10a side as seen from the main surface S1 side of the sensor element 10.

In this case, as shown in FIG. 6A, the first tip 10a of the sensor element 10 is deviated from the designed axis center position of the sensor element 10, which is indicated by a dashed line L1, due to the sensor element 10 warping. For this reason, in fitting the through hole 8bh of the ceramic supporter 8b with the first tip 10a, the ceramic supporter 8b needs to be positioned correspondingly to the position of the first tip 10a. The posture of the ceramic supporter 8b also needs to be adjusted correspondingly to the direction of the first tip 10a, depending on the situation. In other words, control of positioning tends to become complex in the conventional first assembly step.

As shown in FIG. 6A, when w1 and w2 denote the inside dimension of the through hole 8bh of the ceramic supporter 8b and the width on the main surface S1 of the sensor element 10, respectively, the inside dimension w1 is naturally set to a value larger than the width w2 of the sensor element 10.

However, when w3 denotes a maximum width actually occupied by the warping sensor element 10 in the horizontal direction, the ceramic supporter 8b is caught in between in the sensor element 10 if a difference between w3 and w1 is small even though the value of w3 falls within the predetermined dimensional tolerance, as shown in FIG. 6B. This may result in a case where the ceramic supporter 8b is not annularly mounted well.

This may happen similarly on the side surface S2 side of the sensor element 10. In such a case, the ceramic supporter 8b may stay at a height position different from its original position, leading to a malfunction in which a gap is caused with the powder compact 9a annularly mounted last or other members cannot be annularly mounted at predetermined positions. In other words, the first assembly step cannot be completed normally.

As shown in FIG. 6C, once the ceramic supporter 8b is fitted while being tilted horizontally in accordance with the shape of the sensor element 10, the ceramic supporter 8b may be accordingly annularly mounted at its original height position. However, such a state is not always achieved but merely happens by accident.

The above also holds true for the other ceramic supporters 8 and powder compacts 9, not limited to the ceramic supporter 8b. In particular, the shape of the powder compact 9 may be lost due to an impact caused when the powder compact 9, which is fragile, is caught in the sensor element 10 while being annularly mounted.

In other words, the conventional first assembly step has a problem that a malfunction tends to occur when those members are fitted with the first tip 10a of the sensor element 10. The more complicated a warp shape is, the more likely a member is caught while being annularly mounted.

Figure 7A:
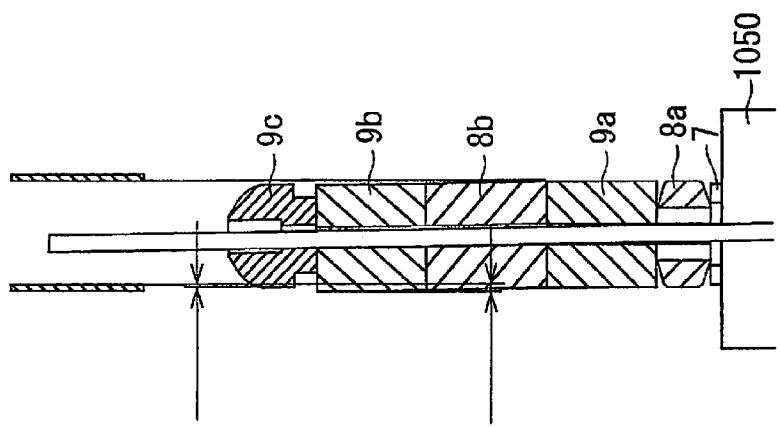
FIGS. 7A and 7B are views schematically showing the intermediate assembly product 20 obtained using the sensor element 10 that warps.
Figure 7B:
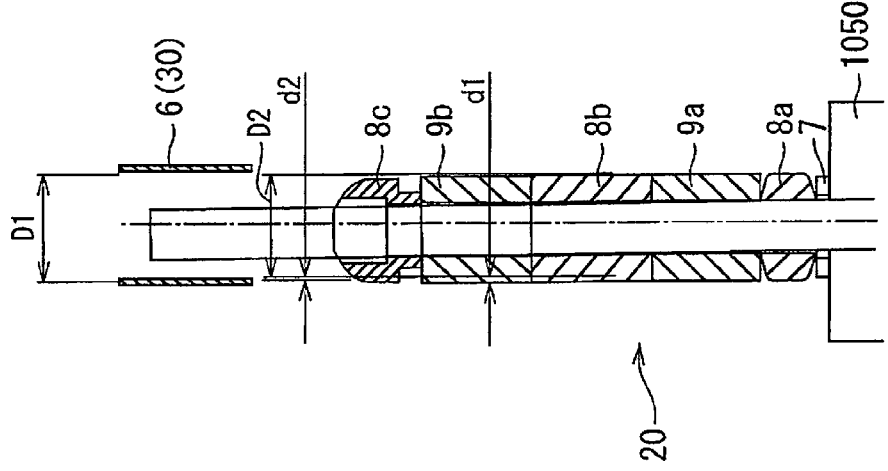

Meanwhile, FIGS. 7A and 7B schematically show the intermediate assembly product 20 obtained in a case where all the members can be annularly mounted to the sensor element 10 in the first assembly step even though the sensor element 10 warps, which includes a case where the member is tilted during annular mounting as shown in FIG. 6C. FIG. 7A is a view in a case where the sensor element 10 is viewed from the main surface S1 side, while FIG. 7B is a view in a case where the sensor element 10 is viewed from the side surface S2 side in the longitudinal direction.

As shown in FIGS. 7A to 7C, in the intermediate assembly product 20, each member annularly mounted is positioned to be displaced horizontally, in accordance with the warp shape of the sensor element 10. In the case shown in FIGS. 7A to 7C, the member arranged at an upper position (closer to the second tip 10b) is displaced more.

In such a case, when D2 (see FIG. 4) denotes the designed outside diameter of the intermediate assembly product 20, the substantial outside diameter of the intermediate assembly product 20 when being fitted into the tubular body 30 in the second assembly step is D2+d1 at the powder compact 9b and is D2+d2 at the ceramic supporter 8c due to a displacement of the member, as shown in FIGS. 7A to 7C. In consideration of a dimensional error of the outside diameter of the intermediate assembly product 20, the inside diameter D1 of the inner tube 6 (tubular body 30) is set to be larger than the design value D2 of the intermediate assembly product 20. However, values of D2+d1 and D2+d2 larger than D1 do not allow the intermediate assembly product 20 and tubular body 30 to be fitted in the second assembly step.

As described above, in conventional case, a warp of the sensor element 10 is likely to result in a case in which the intermediate assembly product 20 is not assembled preferably in the first assembly step or the finished assembly product 40 is not assembled preferably in the second assembly step, as shown in FIGS. 6B and 7A to 7C. In other words, although the sensor element 10 itself is not a defective, the intermediate assembly product 20 or finished assembly product 40 tends to be a defective. This is a factor that reduces the manufacturing yield of the gas sensor 1.

This problem seems to be solved by setting a dimensional tolerance of each member in fitting large. In such setting, however, even if annular mounting can be performed per se, a gap between the sensor element 10 and each member annularly mounted thereto and a gap between the intermediate assembly product 20 and the tubular body 30 become large. As a result, airtightness cannot be secured sufficiently if hermitic sealing is performed through compressing of the powder compacts 9. Therefore, a measure to increase a dimensional tolerance is not practical in terms of securing the performance of the gas sensor 1.

<Holding of Sensor Element in Assembly Steps>

Next, before describing the first assembly step and second assembly step carried out in this embodiment, description is given of how the sensor element 10 is held in the assembly steps, particularly, in the first assembly step. FIGS. 8A, 8B, 9A, 9B, 10A and 10B are view describing how the sensor element 10 is held.

FIGS. 8A and 8B are plan views showing the outline of the holder 50 for use in the first assembly step and second assembly step in this embodiment. As shown in FIG. 8A, a recess 50a into which the sensor element 10 (more specifically, the second tip 10b side thereof) is inserted is provided vertically downward from the upper surface side in the holder 50. Within the holder 50 is provided a first clamp 51 having a sandwiching surface 51s that extends vertically and freely sandwiching or releasing the second tip 10b of the sensor element 10 inserted into the recess 50a, by an operating mechanism (not shown). FIG. 8A shows the state in which the first clamp 51 does not sandwich the sensor element 10, while FIG. 8B shows the state in which the first clamp 51 sandwiches the sensor element 10. In the state in which the second tip 10b side of the sensor element 10 is merely inserted into the recess 50a and is not clamped, the sensor element 10 has an unstable posture and tends to rattle.

While FIGS. 8A and 8B illustrate the case in which the first clamp 51 is provided so as to freely advance and retract in the diagonal direction of the cross-section of the sensor element 10 as indicated by arrows AR3, a specific configuration of the first clamp 51 is not limited to the above.

FIGS. 9A, 9B, 10A and 10B show the state in which the sensor element 10 is held in the first assembly step. In this embodiment, a second clamp 52 shown in FIGS. 9A, 9B, 10A and 10B as well as the first clamp 51 included in the holder 50 described above are used as the means for holding the sensor element 10 in the first assembly step. Sandwiching the sensor element 10 by the first clamp 51 and second clamp 52 described below is also merely referred to as "clamping" below.

Figure 9A:
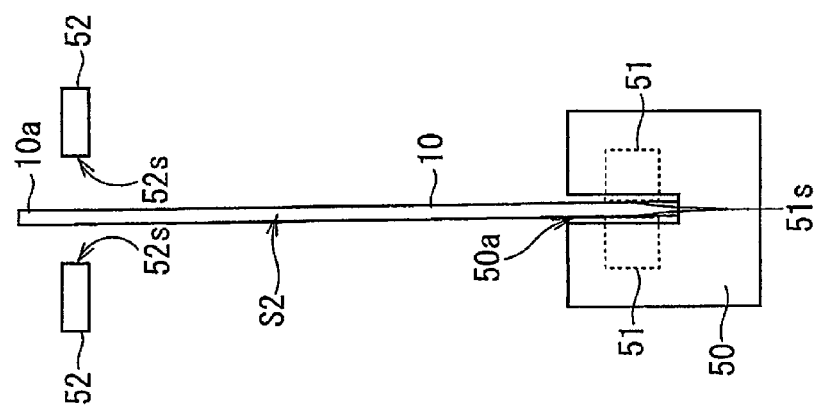
FIGS. 9A and 9B are views showing a state in which the sensor element 10 is held in the first assembly step.
Figure 9B:
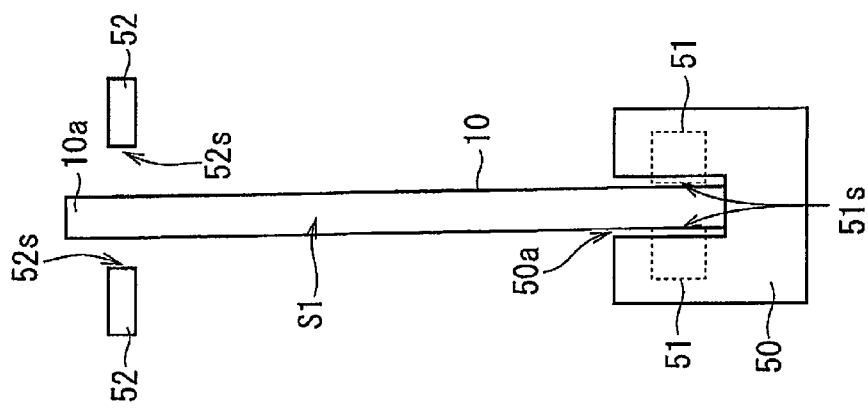
Figure 10A:
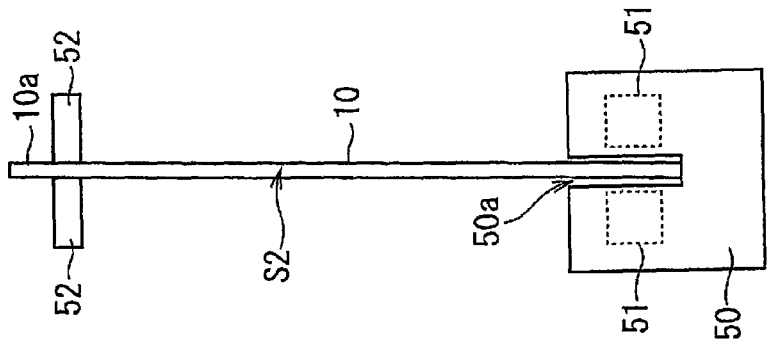
FIGS. 10A and 10B are views showing a state in which the sensor element 10 is held in the first assembly step.
Figure 10B:
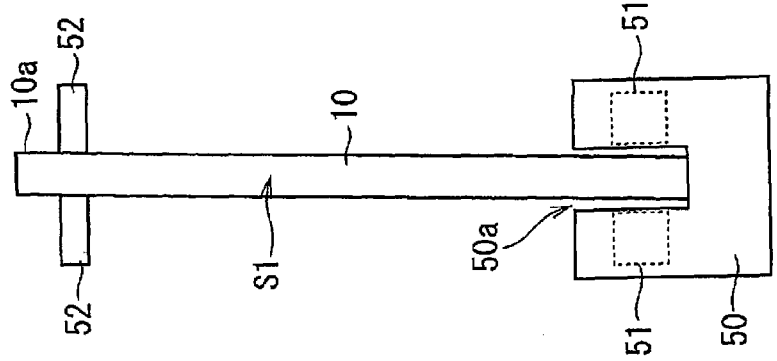

FIGS. 9A and 10A are views in a case where the sensor element 10 clamped by the first clamp 51 or second clamp 52 is viewed from the main surface S1 side, while FIGS. 9B and 10B are views in a case where the sensor element 10 is viewed from the side surface S2 side in the longitudinal direction.

It suffices that the second clamp 52 is provided to be positioned near the first tip 10a of the sensor element 10 when the second tip 10b of the sensor element 10 is inserted into the holder 50. Though not shown in FIGS. 9A, 9B, 10A and 10B, the second clamp 52 is supported by predetermined support means, has a sandwiching surface 52s extending vertically, and is configured to freely sandwich and release the first tip 10a of the sensor element 10 by an operating mechanism (not shown). The second clamp 52 is preferably provided to freely move and down in the vertical direction. While FIGS. 9A, 9B, 10A and 10B show the second clamp 52 to be divided into four members, the configuration thereof is not limited to the above.

In this embodiment, in principle, any one of the first clamp 51 and second clamp 52 clamps the sensor element 10. Specifically, as shown in FIGS. 9A and 9B, the second clamp 52 is apart from the first tip 10a in a case where the first clamp 51 clamps the second tip 10b. This is referred to as a lower-side clamped state (lower-side held state). Meanwhile, as shown in FIGS. 10A and 10B, the first clamp 51 is apart from the second tip 10b in a case where the second clamp 52 clamps the first tip 10a. This is referred to as an upper-side clamped state (upper-side held state).

In the lower-side clamped state, as shown in FIGS. 9A and 9B, when being sandwiched between the sandwiching surface 51s of the first clamp 51 extending vertically, the sensor element 10 is held such that at least the portion near the second tip 10b extends vertically. The sensor element 10, which is warping, is held so as to be deviated more from the vertical direction as becoming closer to the first tip 10a. This is similar to the state in which the sensor element 10 is held in the conventional assembly step shown in FIGS. 5A and 5B.

Meanwhile, in the upper-side clamped state, as shown in FIGS. 10A and 10B, when being sandwiched between the sandwiching surface 52s of the second clamp 52 extending vertically, the sensor element 10 is held such that at least the first tip 10a is held to extend vertically. The sensor element 10, which is warping, is held so as to be deviated more from the vertical direction as becoming closer to the second tip 10b. While the sensor element 10 is in the upper-side clamped state, the second tip 101) is restrained in the recess 50a in such a sense that it remains in the recess 50a provided in the holder 50, but is not sandwiched by the first clamp 51 and thus is not held and fixed in the recess 50a.

<Outline of First Assembly Step>

In this embodiment, the first assembly step is performed through switching between the lower-side clamped state and upper-side clamped state described above at a predetermined timing. Specifically, the sensor element 10 is held in the upper-side clamped state in which through holes of the respective members are fitted with the first tip 10a of the sensor element 10, whereas the sensor element 10 is held in the lower-side clamped state in which the members are respectively arranged at predetermined positions.

FIG. 11 is a view showing, as an example of annularly mounting the members to the sensor element 10, a state in which the through hole 8bh of the ceramic supporter 8b is fitted with the first tip 10a of the sensor element 10 in the upper-side clamped state, which shows the sensor element 10 viewed from the main surface S1 side.

In the upper-side clamped state, the first tip 10a of the sensor element 10 is arranged along the vertical direction as shown in FIG. 11, so that the axis center position of the first tip 10a, which is indicated by a dashed line L2, coincides with the extending direction of the first tip 10a. For this reason, it suffices that in fitting of the ceramic supporter 8b, the ceramic supporter 8b is arranged such that the axial center of the through hole 8bh of the ceramic supporter 8b coincides with the dashed line L2. In such a case, the posture of the ceramic supporter 8b needs not to be adjusted in accordance with a warp.

Moreover, in this case, the maximum width in the horizontal direction of the ceramic supporter 8b is the width w2 on the main surface S1 of the sensor element 10, and accordingly, the through hole 8bh is fitted with the first tip 10a if the width w2 and the inside dimension w1 of the through hole 8bh of the ceramic supporter 8b satisfy a predetermined dimensional tolerance.

From another perspective, differently from the conventional assembly step illustrated in FIGS. 6A to 6C, it is not required to make a high estimate of the maximum width actually occupied by the first tip 10a of the sensor element 10 in the horizontal direction, thereby limiting the dimensional tolerance between the inside dimension w1 and width w2 to a value smaller than before. This is more effective in improving the airtightness of the gas sensor 1.

After the through hole 8bh is fitted with the first tip 10a as described above, the manner of holding the sensor element 10 is switched from the upper-side clamped state to the lower-side clamped state. FIGS. 12A to 12C are conceptual diagrams showing a state during switching of the clamped state. FIGS. 12A to 12C are just conceptual diagrams and show the warp of the sensor element 10 in an exaggerated manner but, in actuality, the ceramic supporter 8b does not reach the second tip 10b.

In a case where the sensor element 10 warps, the posture of the sensor element 10 changes from the upper-side clamped state shown in FIG. 12A to the intermediate state shown in FIG. 12B to the lower-side clamped state shown in FIG. 12C in a short period of time for switching from the upper-side clamped state to the lower-side clamped state. The part along the vertical direction in the sensor element 10 shifts from the first tip 10a to the second tip 10b, and the direction of this shifting coincides with the moving direction of the ceramic supporter 8b fitted with the first tip 10a. Thus, the ceramic supporter 8b moves downward while keeping the state in which the through hole 8bh thereof is located at a part along the vertical direction in the sensor element 10. As a result, the ceramic supporter 8b smoothly reaches a predetermined annularly mounting position if the sensor element 10 warps. The sensor element 10 is held in a posture to be positioned more vertically as the sensor element 10 warps less in both of the upper-side clamped state and lower-side clamped state, and accordingly, the ceramic supporter 8b fitted is annularly mounted more smoothly without being caught in between. For example, the ceramic supporter 8b may reach the predetermined annularly mounting position as soon as the upper-side clamped state is released.

The above also holds true for the other ceramic supporters 8 and powder compacts 9. In other words, in this embodiment, the sensor element 10 is held in the lower-side clamped state in which the through holes of the respective members are fitted and the sensor element 10 is switched to the upper-side clamped state after the members are fitted, so that the ceramic supporters 8 and the powder compacts 9 are annularly mounted to the sensor element 10 with reliability while limiting the dimensional tolerance between the sensor element 10 and the ceramic supporter 8 or powder compact to a small value. Consequently, the intermediate assembly product 20 can be obtained.

<Details of First Assembly Step>

Next, description is given of a flow of the more detailed process of the first assembly step in this embodiment, which is performed based on the above-mentioned principle. In the following description, the warp of the sensor element 10 is confined within such a range that the upper-side clamped state described above is achieved. The following description is not targeted for the sensor element 10 warping to such an extent that the vertical state of the first tip 10a cannot be compatible with the constraint of the second tip 10b in the recess 50a.

FIGS. 13A to 13D, 14A to 14D, 15A to 15D, 16A and 16B, 17A and 17B, and 18A and 18B are views specifically showing the state during the first assembly step. Although FIGS. 13A to 13D, 14A to 14D, 15A to 15D, 16A and 16B, 17A and 17B, and 18A and 18B show the sensor element 10 not warping for the sake of convenience, in actuality, a warp is tolerated in such a range as to allow for the upper-side clamped state as described above.

First, the washer 7 is annularly mounted to the sensor element 10. FIGS. 13A to 13D are views showing the state in which the washer 7 is annularly mounted.

First, as shown in FIG. 13A, with the second tip 10b being inserted in the recess 50a of the holder 50, the sensor element 10 is held in the upper-side clamped state. In this state, predetermined transport means 61 arranges the washer 7 such that the through hole 7h is positioned on the extension of the first tip 10a of the sensor element 10. Although FIG. 13A illustrates the state in which the transport means 61 transports the washer 7 while supporting the washer 7 from below, the manner of transporting the washer 7 is not limited thereto.

The transport means 61 is moved down from this state. Then, as shown in FIG. 13B, the transport means 61 is promptly retracted horizontally as soon as the through hole 7h is fitted with the sensor element 10. As a result, as shown in FIG. 13C, the washer 7 falls onto the second clamp 52 that sandwiches the sensor element 10 while being guided by the sensor element 10.

Then, from this state, the manner of holding the sensor element 10 is switched from the upper-side clamped state to the lower-side clamped state. Consequently, with a release of the sandwiching of the sensor element 10 by the second clamp 52, the washer 7 falls down while being guided by the sensor element 10, and then stops on an upper surface 50s of the holder 50. FIG. 13D shows this state. Through the above, the washer 7 is fitted with the sensor element 10. The through hole 7h of the washer 7 is generally provided to have such a size as not to cause a fear that the through hole 7h may be caught by the sensor element 10, and thus, the washer 7 can be annularly mounted without any trouble.

Next, the ceramic supporter 8a is annularly mounted. FIGS. 14A to 14D are views showing the state in which the ceramic supporter 8a is annularly mounted.

First, as shown in FIG. 14A, the manner of holding the sensor element 10 is switched from the lower-side clamped state to the upper-side clamped state. Then, predetermined transport means 62 arranges the ceramic supporter 8a such that the through hole 8ah is positioned on the extension of the first tip 10a of the sensor element 10. Although FIG. 14A illustrates the state in which the transport means 62 transports the ceramic supporter 8a while gripping the ceramic supporter 8a from its sides, the manner of transporting the ceramic supporter 8a is not limited thereto.

The transport means 62 is moved down from this state. Then, as shown in FIG. 14B, the transport means 62 is promptly retracted horizontally as soon as the through hole 8ah is fitted with the sensor element 10. As a result, as shown in FIG. 14C, the ceramic supporter 8a falls onto the second clamp 52 that sandwiches the sensor element 10, while being guided by the sensor element 10.

Then, from this state, the manner of holding the sensor element 10 is switched from the upper-side clamped state to the lower-side clamped state. Consequently, with a release of the sandwiching of the sensor element 10 by the second clamp 52, the ceramic supporter 8a falls down while being guided by the sensor element 10, and then stops on the washer 7 to be stacked thereon. FIG. 14D shows this state. Through the above, the ceramic supporter 8a is annularly mounted to the sensor element 10.

Then, the powder compact 9a is annularly mounted. FIGS. 15A to 15D are views showing the state in which the powder compact 9a is annularly mounted.

First, as shown in FIG. 15A, the manner of holding the sensor element 10 is switched from the lower-side clamped state to the upper-side clamped state. Then, predetermined transport means 63 arranges the powder compact 9a such that the through hole 9ah is positioned on the extension of the first tip 10a of the sensor element 10. The powder compact 9a, which is fragile, is preferably transported by being adsorb and fixed to the transport means 63 from the above, as shown in FIG. 15A. Alternatively, other transport manner is adoptable as long as the powder compact 9a can be transported without damage.

Then, the transport means 63 is moved down from this state and, as shown in FIG. 15B, the powder compact 9a is placed on the second clamp 52 with the through hole 9ah being fitted with the sensor element 10. The transport means 63 is promptly retracted immediately after the powder compact 9a is placed on the second clamp 52. Then, the second clamp 52 on which the powder compact 9a is placed are moved down along the sensor element 10. In consideration of the warp existing in the sensor element 10, in this moving down, it is preferable to slightly loosen the sandwiching of the sensor element 10 by the second clamp 52, thereby preventing a friction to be caused between the sensor element 10 and the second clamp 52.

As shown in FIG. 15C, moving down of the second clamp 52 is stopped as soon as the second clamp 52 approaches the ceramic supporter 8a and, at the same time, the manner of holding the sensor element 10 is switched to the lower-side clamped state. As a result, the powder compact 9a falls down for the remaining distance up to the ceramic supporter 8a while being guided by the sensor element 10, and is then stopped to be stacked on the ceramic supporter 8a. FIG. 15D shows this state. Through the above, the powder compact 9a is annularly mounted to the sensor element 10. The second clamp 52 promptly returns to the original position as soon as switching is made to the lower-side clamped state.

The reason why the second clamp 52 is moved down in the case where the powder compact 9a is annularly mounted, unlike the case in which the washer 7 or ceramic supporter 8a is annularly mounted, is to minimize damage to the powder compact 9a by, even slightly, reducing a falling distance of the powder compact 9a. Such a manner does not always need to be employed as long as the powder compact 9a can be annularly mounted without damage.

Then, the ceramic supporter 8b, powder compact 9b, and ceramic supporter 8c are annularly mounted in order. It suffices that this annular mounting is performed similarly to the annular mounting of the ceramic supporter 8a or powder compact 9a described above.

FIGS. 16A and 16B are views showing the state in which the ceramic supporter 8b is annularly mounted. In other words, as shown in FIG. 16A, the manner of holding the sensor element 10 is switched from the lower-side clamped state to the upper-side clamped state. Then, predetermined transport means 64 arranges the ceramic supporter 8b such that the through hole 8bh is positioned on the extension of the first tip 10a of the sensor element 10. Then, the transport means 64 is moved down from this state, and then, the transport means 64 is promptly retracted horizontally as soon as the through hole 8bh is fitted with the sensor element 10. Through the above, the ceramic supporter 8b is caused to fall onto the second clamp 52, and then, the manner of holding the sensor element 10 is switched from the upper-side clamped state to the lower-side clamped state such that the ceramic supporter 8b is caused to fall down to be stacked on the powder compact 9a while being guided by the sensor element 10. As a result, as shown in FIG. 16B, the ceramic supporter 8b is annularly mounted to the sensor element 10.

FIGS. 17A and 17B are views showing the state in which the powder compact 9b is annularly mounted. In other words, as shown in FIG. 17A, the manner of holding the sensor element 10 is switched from the lower-side clamped state to the upper-side clamped state. Then, predetermined transport means 65 arranges the powder compact 9b such that the through hole 9bh is positioned on the extension of the first tip 10a of the sensor element 10. Also, the powder compact 9b is preferably transported by being adsorb and fixed to the transport means 65 from above as shown in FIG. 17A, as in the case of the powder compact 9a. Then, the transport means 63 is moved down from this state, so that the powder compact 9b is placed on the second clamp 52 with the through hole 9bh being fitted with the sensor element 10. After that, the second clamp 52 on which the powder compact 9b is placed is moved down along the sensor element 10. As soon as the second clamp 52 approaches the ceramic supporter 8b, moving down of the second clamp 52 is stopped and, at the same time, the manner of holding the sensor element 10 is switched to the lower-side clamped state, causing the powder compact 9b to fall down onto the ceramic supporter 8b. The powder compact 9b stops to be stacked thereon. This allows the ceramic supporter 8b to be annularly mounted to the sensor element 10 as shown in FIG. 17B.

Figure 18A:
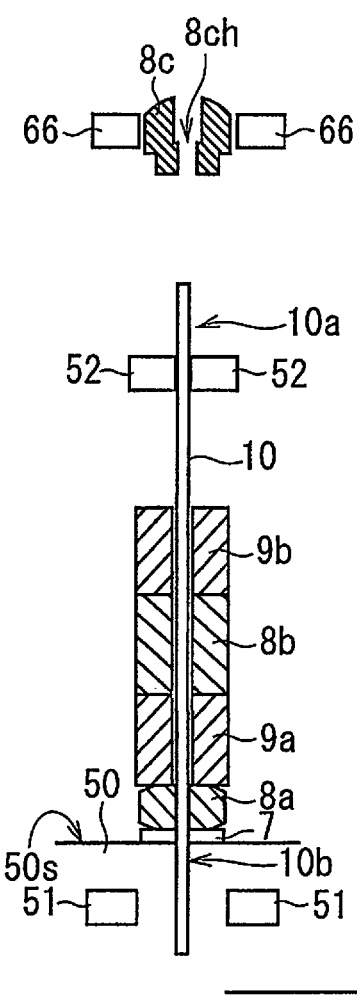
FIGS. 18A and 18B are views showing a state in which a ceramic supporter 8$c$ is annularly mounted.
Figure 18B:
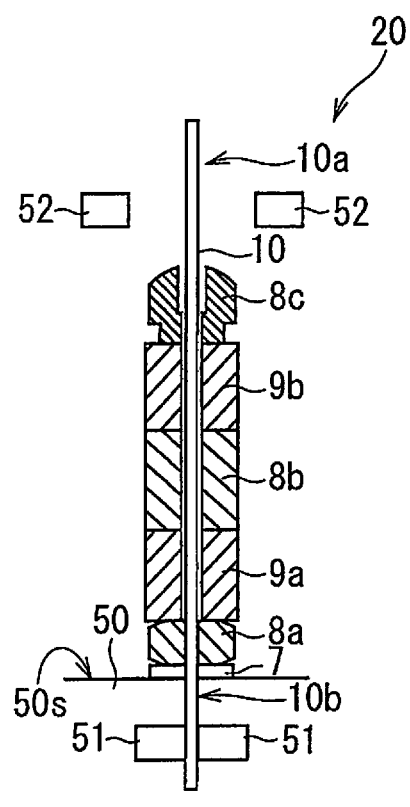

FIGS. 18A and 18B are views showing the state in which the ceramic supporter 8c is annularly mounted. In other words, as shown in FIG. 18A, the manner of holding the sensor element 10 is switched from the lower-side clamped state to the upper-side clamped state. Then, predetermined transport means 66 arranges the ceramic supporter 8c such that the through hole 8ch is positioned on the extension of the first tip 10a of the sensor element 10. Then, the transport means 66 is moved down from this state and is promptly retracted horizontally as soon as the through hole 8ch is fitted with the sensor element 10. Through the above, the ceramic supporter 8c is caused to fall onto the second clamp 52, and then, the manner of holding the sensor element 10 is switched from the upper-side clamped state to the lower-side clamped state such that the ceramic supporter 8c is caused to fall down to be stacked on the powder compact 9a while being guided by the sensor element 10. As a result, as shown in FIG. 18B, the ceramic supporter 8c is annularly mounted to the sensor element 10. The ceramic supporter 8c has been annularly mounted, so that the intermediate assembly product 20 is obtained.

<Second Assembly Step>

Next, the second assembly step is described. As described above, the conventional second assembly step is problematic in that as shown in FIGS. 7A and 7B, the substantial outside diameter of the intermediate assembly product 20 when being fitted with the tubular body 30 in the second assembly step is larger than the inside diameter D1 of the tubular body 30 due to the warp of the sensor element 10. In this embodiment, therefore, the intermediate assembly product 20 and the tubular body 30 are fitted together with the substantial outside diameter of the intermediate assembly product 20 being minimized (being made closer to the design value D2 as much as possible).

Figure 19A:
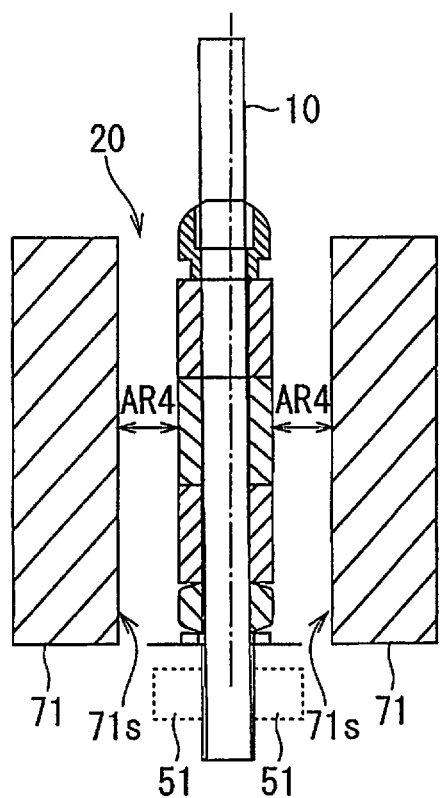
FIGS. 19A and 19B are views showing a state in start of the second assembly step.
Figure 19B:
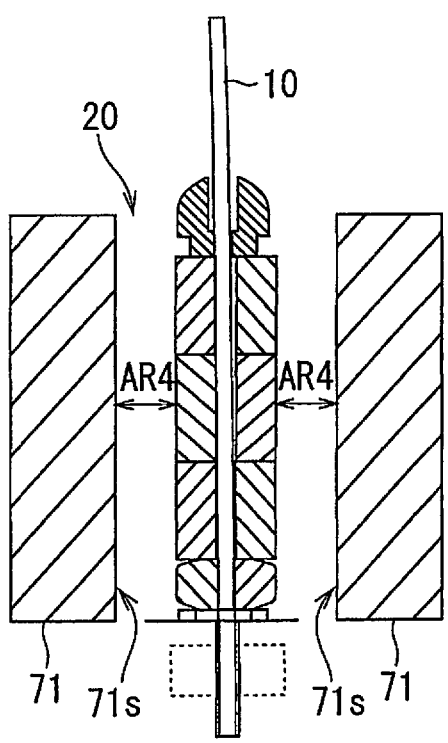

FIGS. 19A and 19B are views showing the state in which the second assembly step is started. FIG. 19A is a view in a case where the sensor element 10 is viewed from the main surface S1 side, whereas FIG. 19B is a view in a case where the sensor element 10 is viewed from the side surface S2 side.

In other words, FIGS. 19A and 19B show the state after the ceramic supporter 8c is annularly mounted to obtain the intermediate assembly product 20. In this case, the sensor element 10 forming the intermediate assembly product 20 is in the lower-side clamped state. For this reason, in the intermediate assembly product 20, the member arranged more upward (closer to the second tip 10b) is positioned to be displaced more horizontally in accordance with the warping shape of the sensor element 10, as in the conventional case shown in FIGS. 7A and 7B.

In this embodiment, prior to fitting with the tubular body 30, the centering process using a centering guide 71 is performed on the intermediate assembly product 20 being in the state as shown in FIGS. 19A and 19B.

It suffices that as shown in FIGS. 19A and 19B, the centering guide 71 is provided so as to extend along the intermediate assembly product 20 near the intermediate assembly product 20 in the state in which the intermediate assembly product 20 is assembled and the second tip 10b of the sensor element 10, being a component thereof, is inserted into the holder 50 as it is. The centering guide 71, which is supported by predetermined support means not shown in FIGS. 19A and 19B and has a sandwiching surface 71s extending vertically, is configured to freely advance and retract horizontally as indicated by arrows AR4 through driving by a drive mechanism (not shown). This allows the intermediate assembly product 20 to be freely sandwiched and released from the side surface sides of the respective members annularly mounted. While FIGS. 19A and 19B shows the centering guide 71 to be divided into four members, the configuration thereof is not limited to the above.

Figure 20A:
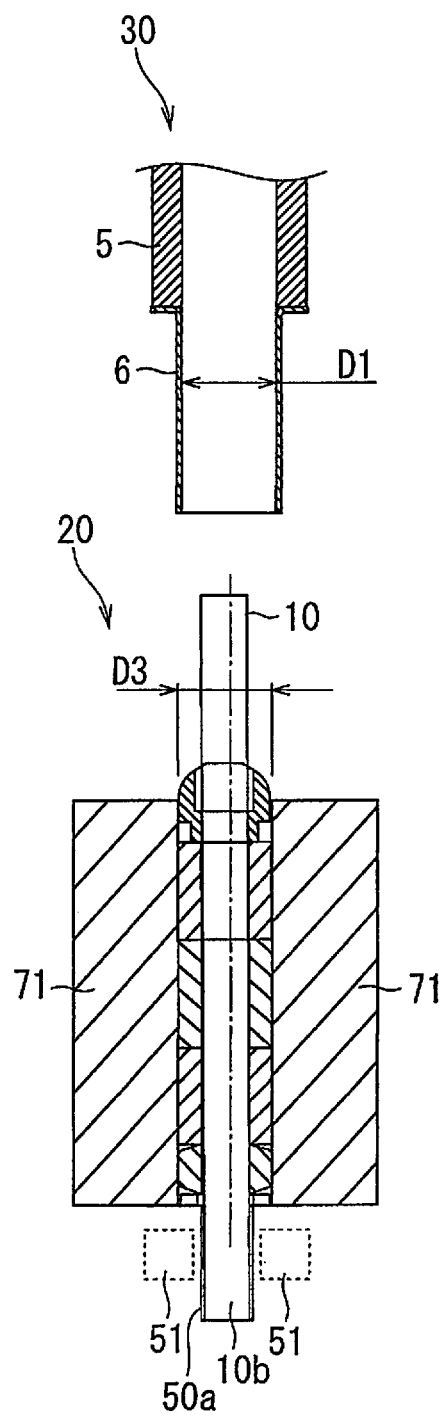
FIGS. 20A and 20B are views showing a state of a centering process using a centering guide 71.
Figure 20B:
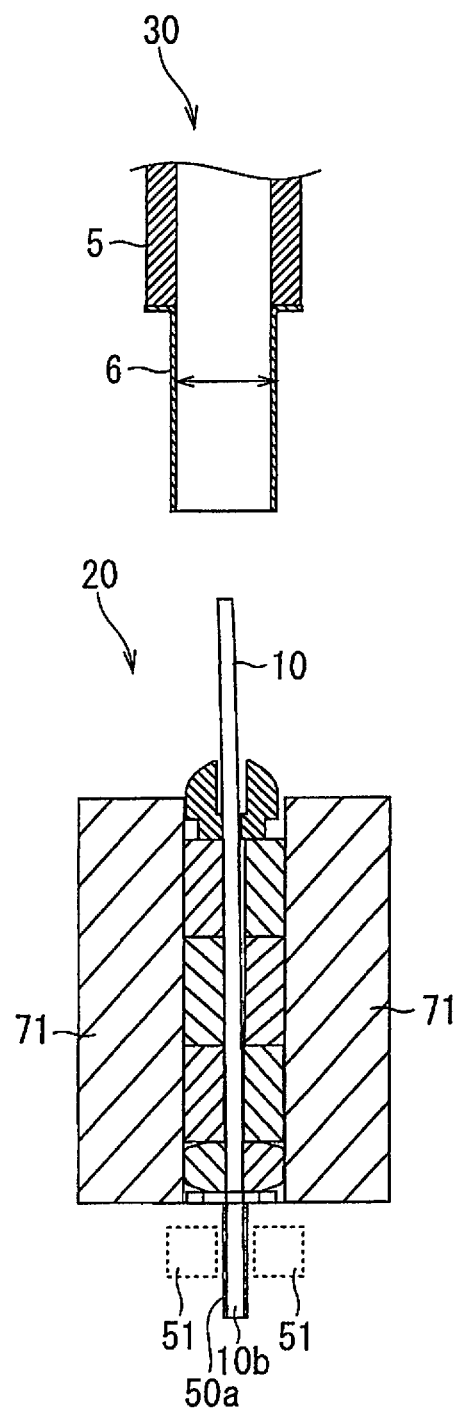

FIGS. 20A and 20B are views showing the state of the centering process using the centering guide 71. FIG. 20A is a view in a case where the sensor element 10 is viewed from the main surface S1 side, whereas FIG. 20B is a view in a case where the sensor element 10 is viewed from the side surface S2 side. FIGS. 21A and 21B are diagrams conceptually showing the posture of the sensor element 10 before and after the centering process. FIGS. 21A and 21B are just conceptual diagrams, which show a warp of the sensor element 10 in an exaggerated manner.

Specifically, as shown in FIGS. 20A and 20B, the lower-side clamped state is released and, at the same time, the centering guide 71 sandwiches the intermediate assembly product 20. In this case, the members annularly mounted to the sensor element 10 among the members constituting the intermediate assembly product 20 experience a horizontal force from the centering guide 71 with which the members being in contact. The members are not restrained horizontally, and are thus displaced up to such a position that the forces from opposite directions are in equilibrium.

In this case, as shown in FIG. 21A, the sensor element 10 also indirectly experiences a horizontal force F from the centering guide 71 via the member that has experienced the horizontal force from the centering guide 71. Although the very second tip 10b is restrained in the recess 50a of the holder 50, the sensor element 10 released from the holding by the first clamp 51 is not fixed to the recess 50a and thus changes its posture with the recess 50a as a fulcrum, from the state before centering shown in FIG. 21A. Specifically, the posture of the sensor element 10 changes toward the state in which a maximum horizontal occupancy width W thereof is minimized, as shown in FIG. 21B.

Consequently, through the centering process, the intermediate assembly product 20 changes from the state in which the sensor element 10 is deviated more from the vertical direction as becoming closer to the upper side and the members annularly mounted are accordingly horizontally displaced more as becoming closer to the upper side, which is as shown in FIGS. 19A and 19B, to the state in which the members fit between the sandwiching surface 71s of the centering guide 71 with the smallest maximum outside diameter D3, which is as shown in FIGS. 20A and 20B. The centering guide 71 retracts horizontally.

In this embodiment, the members constituting the intermediate assembly product 20 are subjected to centering as described above, and then, the intermediate assembly product 20 and the tubular body 30 are fitted together. The maximum outside diameter D3 of the intermediate assembly product 20 in this case normally falls within the range of the dimensional tolerance for the designed value D2 and is a value smaller than the inside diameter D1 of the tubular body 30, allowing for preferred fitting.

The fitting is performed by causing the center line of the intermediate assembly product 20 after the centering process to coincide with the center line of the tubular body 30 and then moving down the tubular body 30 with respect to the intermediate assembly product 20, or, on the contrary, by inserting the intermediate assembly product 20 into the fixed tubular body 30, otherwise, by combining those operations.

From another perspective, this embodiment does not require to make a high estimate of the dimensional tolerance of the maximum outside diameter of the intermediate assembly product 20 with respect to the designed value D2, also limiting the dimensional tolerance of the inside diameter D1 of the tubular body 30 to a value smaller than the conventional one. This is more effective in improving the airtightness of the gas sensor 1.

In other words, in this embodiment, the centering process is performed on the intermediate assembly product 20 obtained by annularly mounting the ceramic supporters 8 and the powder compacts 9 to minimize the outside diameter of the intermediate assembly product 20, and then the tubular body 30 is annularly mounted. This reliably enables annular mounting of the tubular body 30 to the intermediate assembly product 20 while limiting the dimensional tolerance between the intermediate assembly product 20 and tubular body 30 to a small value, to thereby obtain the finished assembly product 40.

<Outline of Assembly Apparatus>

Figure 22:
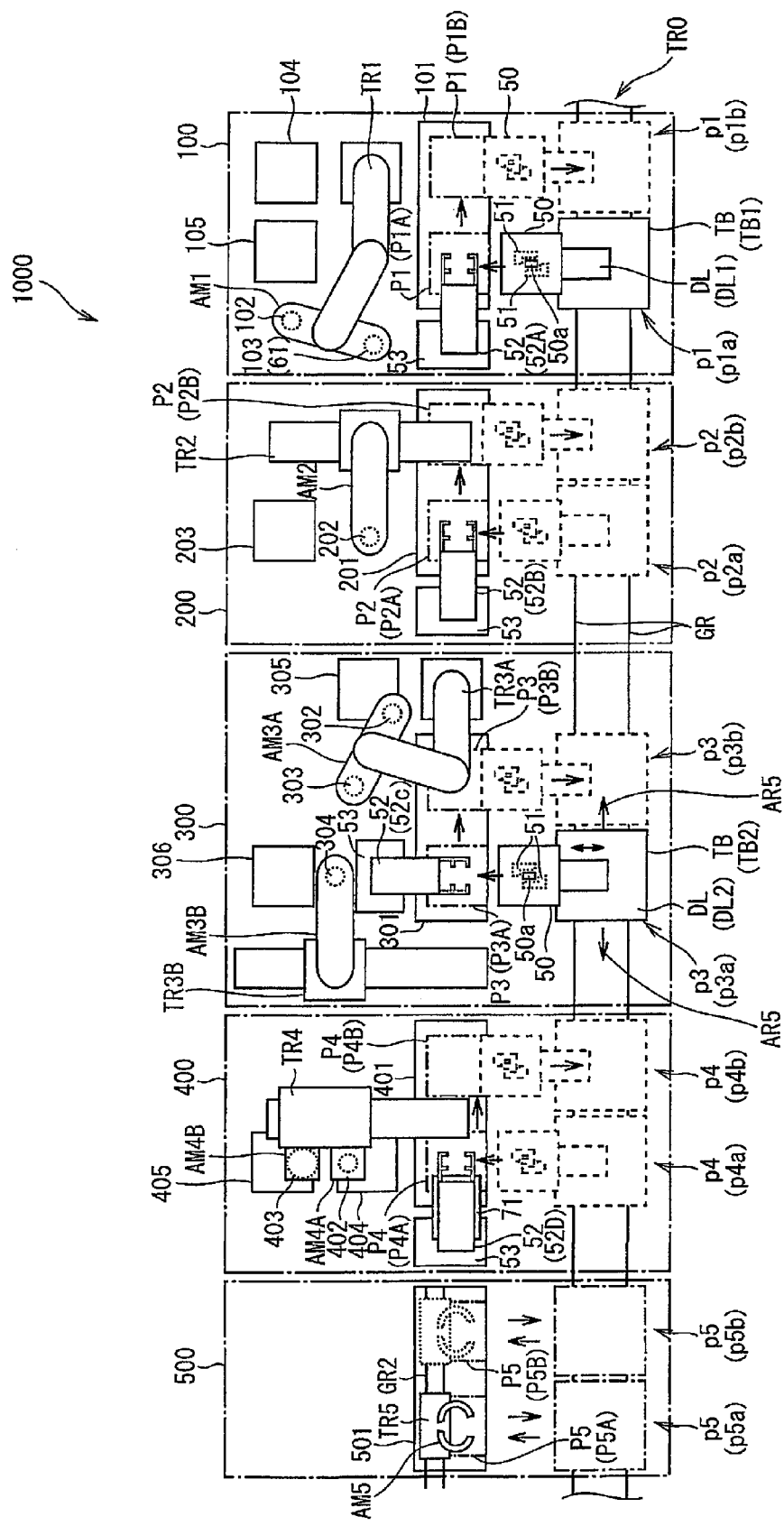
FIG. 22 is a plan view of an assembly apparatus 1000 that performs the first assembly step and second assembly step.

Next, an example of an apparatus for use in the assembly steps described above is described. FIG. 22 is a plan view of an assembly apparatus 1000 that performs the first assembly step and second assembly step in this embodiment.

In outline, the assembly apparatus 1000 has a configuration including a first zone 100, a second zone 200, a third zone 300, a fourth zone 400, and a fifth zone 500 horizontally lined up in this order. In the first zone 100, the sensor element 10 is inserted into the holder 50 and the washer 7 is annularly mounted. In the second zone 200, the ceramic supporter 8a is annularly mounted. In the third zone 300, the ceramic supporter 8b and the powder compacts 9a and 9b are annularly mounted. In the fourth zone 400, the ceramic supporter 8c is annularly mounted and the tubular body 30 is annularly mounted to the intermediate assembly product 20 obtained by this annular mounting. In the fifth zone 500, the finished assembly product 40 which has been obtained through the above is transported to the outside of the apparatus.

The assembly apparatus 1000 further includes inter-zone transport means TR0 that transports the holder 50 among the zones. Specifically, the inter-zone transport means TR0 is a linear slider including two moving tables TB (a first moving table TB1 and a second moving table TB2) configured to freely move as indicated by arrows AR5 on a guide rail GR provided so as to cross zones horizontally lined up. In addition, the moving tables TB include deliver means DL (first deliver means DL1 and second deliver means DL2) that exchange the holder 50 among holder arrangement positions P1 to P5 set in holder arrangement portions 101, 201, 301, 401, and 501 included in the respective zones. The deliver means DL are operated with the moving tables TB being stopped at deliver positions p1 to p5 opposed to the holder arrangement positions P1 to P5, allowing for the transfer of the holder 50 between the moving tables TB and the holder arrangement portions 101, 201, 301, 401, and 501.

The holder arrangement portions 101, 201, 301, 401, and 501 include a first clamp operating mechanism (not shown). The first clamp operating mechanism can be connected to the first clamp 51 to operate the first clamp 51 as soon as the holder 50 is arranged at the holder arrangement positions P1 to P5 provided in the respective holder arrangement portions.

The first clamp 51 is preferably configured to operate so as to be opened only in a case where the first clamp operating mechanism performs a particular opening operation and to keep a non-open state in other cases. In short, the non-open state is a state in which the sensor element 10 is sandwiched if it is inserted into the recess 50a. Such a configuration can be achieved using, for example, biasing against the first clamp 51 by a spring.

Meanwhile, the second clamp 52 included in each zone is provided with a second clamp operating mechanism 53 corresponding to those. The second clamp 52 is brought into the sandwiching state by the second clamp operating mechanism 53 only for achieving the above-mentioned upper-side clamped state and are brought into the open state in other cases.

More specifically, the first moving table TB1 serves to transfer the holder 50 mainly among the first zone 100, second zone 200, and third zone 300, whereas the second moving table TB2 serves to transfer the holder 50 mainly among the third zone 300, fourth zone 400, and fifth zone 500.

In the assembly apparatus 1000 configured as described above, the moving operation of the moving table TB by the inter-zone transport means TR0 and the delivering operation of the deliver means DL are appropriately combined. This allows the holder 50 with the recess 50a into which the sensor element 10 is inserted, including the one constituting the intermediate assembly product 20 during assembly or the finished assembly product 40, to be transferred to a target position along with the advancement of the assembly step. This configuration enables the assembly apparatus 1000 to simultaneously perform different stages of assembly processes for varying holders 50 at different locations.

In such a case, the moving table TB after delivering the holder 50 needs not to be on standby at its deliver position in each zone, but can be moved to another position to deliver another holder 50. In other words, the assembly apparatus 1000 can efficiently perform an assembly process.

Hereinbelow, the holder 50 with the recess 50a into which the sensor element 10 is not inserted is referred to as an empty holder 50 irrespective of which the sensor element 10 is in the state before or after assembly. The assembly apparatus 1000 includes control means (not shown) that controls the operation of each portion of the apparatus, and a series of operations descried below proceeds automatically through control of each portion by the control means.

<First Zone>

The first zone 100 includes an articulated-robot-arm-type transfer mechanism TR1 as well as the holder arrangement portion 101. The transfer mechanism TR1 is provided with a distal arm portion AM1. The distal arm portion AM1 can freely move up and down vertically and rotate in the horizontal plane, and includes a sensor element transfer arm 102 and a washer transfer arm 103 (equivalent to the transport means 61 of FIGS. 13A to 13D) at one end and the other end in the longitudinal direction thereof, respectively, which extend vertically. The first zone 100 further includes an element supply portion 104 being a portion that supplies the sensor element 10 to be assembled and a washer supply portion 105 being a portion that supplies the washer 7.

The process in the first zone 100 is started by, first, the first moving table TB1, which transports an empty holder 50, stopping at the deliver position p1 (p1a) and the first deliver means DL1 delivering the holder 50 to the holder arrangement position P1 (P1A).

First, the transfer mechanism TR1 continuously causes the sensor element transfer arm 102 to obtain the sensor element 10 from the element supply portion 104 and the washer transfer arm 103 to obtain the washer 7 from the washer supply portion 105.

Specifically, first, the distal arm portion AM1 is moved down with the sensor element transfer arm 102 being positioned above the element supply portion 104 so that the sensor element transfer arm 102 holds the sensor element 10. After that, the distal arm portion AM1 is once moved up, and then, the distal arm portion AM1 is moved down with the washer transfer arm 103 being positioned above the washer supply portion 105 so that the washer transfer arm 103 holds the washer 7. The distal arm portion AM1 is moved up again after the holding of the washer 7.

Then, the sensor element transfer arm 102 inserts the sensor element 10 to the recess 50a of the empty holder 50 arranged at the holder arrangement position P1 (P1A). Then, for this sensor element 10, the washer transfer arm 103 arranges the washer 7 (placed onto the second clamp 52 (52A)). These operations are performed continuously by appropriately changing the posture of the transfer mechanism TR1 in the horizontal plane.

Subsequently, the washer 7 is annularly mounted to the sensor element 10 in the manner illustrated in FIGS. 13A to 13D. At this time, switching is appropriately made between the lower-side clamped state by the first clamp 51 and the upper-side clamped state by the second clamp 52 (52A).

After the annular mounting of the washer 7, the holder 50 is moved by a drive mechanism (not shown) included in the holder arrangement portion 101 from the holder arrangement position P1A to the holder arrangement position P1 (P1B) adjacent to this. Then, the holder 50 is delivered to the first moving table TB1 by the first deliver means DL1 included in the first moving table TB1 which has been transported to the deliver position p1 (p1b) opposed to the holder arrangement position P1B. The first moving table TB1 on which the holder 50 has been placed is transported to the second zone 200 by the inter-zone transport means TR0.

<Second Zone>

The second zone 200 includes a transfer mechanism TR2 being an orthogonal coordinate robot as well as the holder arrangement portion 201. The transfer mechanism TR2 is provided with an arm portion AM2. The arm portion AM2 is movable horizontally and includes, at one end in the longitudinal direction thereof, a ceramic supporter transfer arm 202 (equivalent to the transport means 62 of FIGS. 14A to 14D) capable of freely moving up and down vertically. The second zone 200 further includes a first ceramic supporter supply portion 203 being a portion that supplies the ceramic supporter 8a.

The process in the second zone 200 is started by, first, the first moving table TB1, which has transported the holder 50 holding the sensor element 10 to which the washer 7 has been annularly mounted, stopping at the deliver position p2 (p2a) and the first deliver means DL1 delivering this holder 50 to the holder arrangement position P2 (P2A).

First, the transfer mechanism TR2 causes the ceramic supporter transfer arm 202 to obtain the ceramic supporter 8a from the first ceramic supporter supply portion 203.

Specifically, the ceramic supporter transfer arm 202 is moved down while being positioned above the first ceramic supporter supply portion 203 so as to hold the ceramic supporter 8a. After the holding of the ceramic supporter 8a, the ceramic supporter transfer arm 202 is moved up again.

Subsequently, the ceramic supporter transfer arm 202 transports the ceramic supporter 8a to above the sensor element 10, and then, the ceramic supporter 8a is annularly mounted to the sensor element 10 in the manner illustrated in FIGS. 14A to 14D. At this time, switching is appropriately made between the lower-side clamped state by the first clamp 51 and the upper-side clamped state by the second clamp 52 (52B) as described above.

After the annular mounting of the ceramic supporter 8a, the holder 50 is moved by a drive mechanism (not shown) included in the holder arrangement portion 201 from the holder arrangement position P2A to the holder arrangement position P2 (P2B) adjacent to this. Then, the holder 50 is delivered to the first moving table TB1 by the first deliver means DL1 included in the first moving table TB1 which has been transported to the deliver position p2 (p2b) opposed to the holder arrangement position P2B. The first moving table TB1 on which the holder 50 has been placed is transported to the third zone 300 by the inter-zone transport means TR0.

<Third Zone>

The third zone 300 includes an articulated-robot-arm-type transfer mechanism TR3A and a transfer mechanism TR3B being an orthogonal coordinate robot as well as the holder arrangement portion 301.

The transfer mechanism TR3A is provided with a distal arm portion AM3A. The distal arm portion AM3A can freely move up and down vertically and freely rotate in the horizontal plane, and includes powder compact transfer arms 302 and 303 (equivalent to the transport means 63 of FIGS. 15A to 15D and the transport means 65 of FIGS. 17A and 17B, respectively) at two ends in the longitudinal direction thereof, which are configured to extend vertically. The powder compact transfer arms 302 and 303 are configured such that the lower ends thereof can adsorb and hold the powder compact 9.

Meanwhile, the transfer mechanism TR3B is provided with an arm portion AM3B. The arm portion AM3B of the transfer mechanism TR3B is configured to freely move horizontally and includes at one end in the longitudinal direction thereof, a ceramic supporter transfer arm 304 (equivalent to the transport means 64 of FIGS. 16A and 16B) capable of freely moving up and down vertically. The third zone 300 includes a powder compact supply portion 305 being the portion that supplies the powder compacts 9a and 9b and a second ceramic supporter supply portion 306 being the portion that supplies the ceramic supporter 8b.

The process in the second zone 300 is started by, first, the first moving table TB1, which has transported the holder 50 holding the sensor element 10 to which the ceramic supporter 8a has been annularly mounted, stopping at the deliver position p3 (p3a) and the first deliver means DL1 delivering this holder 50 to the holder arrangement position P3 (P3A).

First, the transfer mechanism TR3A continuously causes the two powder compact transfer arms 302 and 303 to obtain the powder compacts 9 (9a and 9b) from the powder compact supply portion 305.

Specifically, first, the distal arm portion AM3A is moved down with the powder compact transfer arm 302 being positioned above the powder compact supply portion 305 so as to cause the lower end of the powder compact transfer arm 302 to adsorb the powder compact 9 (9a). After that, the distal arm portion AM3A is moved up once, and then, the distal arm portion AM3A is moved down with the powder compact transfer arm 303 being positioned above the powder compact supply portion 305 so as to cause the lower end of the powder compact transfer arm 303 to adsorb the powder compact 9 (9b). After the holding of the powder compact 9 (9b), the distal arm portion AM3A is moved up again.

Further, the transfer mechanism TR3B causes the ceramic supporter transfer arm 304 to obtain the ceramic supporter 8b from the second ceramic supporter supply portion 306.

Specifically, the ceramic supporter transfer arm 304 is moved down while being positioned above the second ceramic supporter supply portion 306 so as to hold the ceramic supporter 8b. After the holding of the ceramic supporter 8a, the ceramic supporter transfer arm 304 is moved up again.

Subsequently, the powder compact 9a, ceramic supporter 8b, and powder compact 9b are annularly mounted to the sensor element 10 in order in the manner illustrated in FIGS. 15A to 15D, 16A and 16B, and 17A and 17B. In annularly mounting each member, switching is appropriately made between the lower-side clamped state by the first clamp 51 and the upper-side clamped state by the second clamp 52 (52C) as described above.

More specifically, first, the sensor element 10 is brought into the upper-side clamped state, and accordingly, the transfer mechanism TR3A causes the powder compact transfer arm 302 to place the powder compact 9a onto the second clamp 52C sandwiching the sensor element 10. The powder compact 9a placed in the upper-side clamped state is annularly mounted to the sensor element 10 in the above-mentioned manner. In this case, the transfer mechanism TR3A once retracts from near the second clamp 52C.

After the annular mounting of the powder compact 9a, the sensor element 10 is brought into the upper-side clamped state again. Then, the transfer mechanism TR3B for the ceramic supporter 8b causes the ceramic supporter transfer arm 304 to place the ceramic supporter 8b onto the second clamp 52C. The ceramic supporter 8b placed on the second clamp 52C is annularly mounted to the sensor element 10 in the above-mentioned manner. In this case, the transfer mechanism TR3B that has placed the ceramic supporter 8b promptly retracts from near the second clamp 52C.

After the annular mounting of the ceramic supporter 8b, the sensor element 10 is brought into the upper-side clamped state the third time around. The transfer mechanism TR3A accordingly causes the powder compact transfer arm 303 to place the powder compact 9b on the second clamp 52C again. The powder compact 9b placed in the upper-side clamped state is annularly mounted to the sensor element 10 in the above-mentioned manner.

After the annular mounting of the powder compact 9b, the holder 50 is delivered to the second moving table TB2 by the second deliver means DL2 included in the second moving table TB2 which has been transported to the deliver position p3a opposed to the holder arrangement position P3A. The second moving table TB2 on which the holder 50 has been placed is transported to the fourth zone 400 by the inter-zone transport means TR0.

<Fourth Zone>

The fourth zone 400 includes a transfer mechanism TR4 being an orthogonal coordinate robot as well as the holder arrangement portion 401. The transfer mechanism TR4 is provided with a first arm portion AM4A and a second arm portion AM4B. The first arm portion AM4A includes a ceramic supporter transfer arm 402 (equivalent to the transport means 66 of FIGS. 18A and 18B) capable of freely moving up and down vertically. The second arm portion AM4B includes a tubular body transfer arm 403 capable of freely moving up and down vertically as well. The fourth zone 400 further includes a third ceramic supporter supply portion 404 being a portion that supplies the ceramic supporter 8c and a tubular body supply portion 405 being a portion that supplies the tubular body 30. The first arm portion AM4A and second arm portion AM4B are movable in a horizontally integrated manner.

The process in the fourth zone 400 starts by, first, the second moving table TB2, which has transported from the third zone 300 the holder 50 holding the sensor element 10 to which the powder compact 9b has been annularly mounted, stopping at the deliver position p4 (p4a), and then, the second deliver means DL2 delivering the holder 50 to the holder arrangement position P4 (P4A).

First, the transfer mechanism TR4 causes the ceramic supporter transfer arm 402 to obtain the ceramic supporter 8c from the third ceramic supporter supply portion 404. Specifically, the ceramic supporter transfer arm 402 is moved down while being positioned above the third ceramic supporter supply portion 404 and is caused to hold the ceramic supporter 8c. After the holding of the ceramic supporter 8c, the ceramic supporter transfer arm 402 is moved up again.

Then, the transfer mechanism TR4 also causes the tubular body transfer arm 403 to obtain the tubular body 30 from the tubular body supply portion 405. Specifically, the tubular body transfer arm 403 is moved down while being positioned above the tubular body supply portion 405 and is caused to hold the tubular body 30. After holding of the tubular body 30, the tubular body transfer arm 403 is moved up again.

Then, the ceramic supporter 8c is transported to above the sensor element 10 by the ceramic supporter transfer arm 402, and the ceramic supporter 8c is annularly mounted to the sensor element 10 in the manner illustrated in FIGS. 18A and 18B. At that time, switching is appropriately made between the lower-side clamped state by the first clamp 51 and the upper-side clamped state by the second clamp 52 (52D) as described above.

The intermediate assembly product 20 is obtained through the annular mounting of the ceramic supporter 8c, and then, centering guide 71 performs the centering process on the intermediate assembly product 20 in the manner illustrated in FIGS. 19A, 19B, 20A, and 20.

Then, the tubular body 30 is transported by the tubular body transfer arm 403 to above the intermediate assembly product 20 after the centering process, and the tubular body 30 is annularly mounted to the intermediate assembly product 20. As a result, the finished assembly product 40 is obtained.

After the finished assembly product 40 has been obtained, the holder 50 is moved from the holder arrangement position P4A to the holder arrangement position P4 (P4B) adjacent to this by a drive mechanism (not shown) included in the holder arrangement portion 401. Then, the holder 50 is delivered to the second moving table TB2 by the second deliver means DL2 included in the second moving table TB2 which has been transported to the deliver position p4 (p4b) opposed to the holder arrangement position P4B. The second moving table TB2 on which the holder 50 has been placed is transported to the fifth zone 500 by the inter-zone transport means TR0.

<Fifth Zone>

The fifth zone 500 includes a finished product transport mechanism TR5, which can freely move horizontally along a guide rail GR2 and transports the finished assembly product 40 held by the holder 50 after the insertion of the sensor element 10 into the recess 50a to the outside the apparatus, as well as the holder arrangement portion 501. The finished product transport mechanism TR5 is provided with an arm portion AM5 capable of freely moving up and down vertically.

In the fifth zone 500, the second moving table TB2 that has transported the holder 50 holding the finished assembly product 40 from the fourth zone 400 stops at the deliver position p5 (p5a or p5b), whereby the holder 50 is delivered to the holder arrangement position P5 (P5A or P5B) by the second deliver means DL2. The holder 50 holding the finished assembly product 40 is alternately delivered to the holder arrangement position P5A and holder arrangement position P5B.

At the holder arrangement position P5A or P5B, the finished product transport mechanism TR5 causes the arm portion AM5 to sandwich the finished assembly product 40 and further moves up the arm portion AM5, thereby obtaining the finished assembly product 40 from the holder 50. The finished product transport mechanism TR5 sandwiching the finished assembly product 40 by the arm portion AM5 delivers the finished assembly product 40 to the outside of the apparatus along the guide rail GR2.

The holder 50 that has no finished assembly product 40 and becomes empty again is delivered to the second moving table TB2, which has been transported to the deliver position p5a or p5b opposed to the holder arrangement position P5A or P5B, by the second deliver means DL2 included in the second moving table TB2.

Then, the second moving table TB2 on which the empty holder 50 has been placed is transported up to the deliver position p3b of the third zone 300 by the inter-zone transport means TR0. The second moving table TB2 stops at the deliver position p3b, so that the empty holder 50 placed on the second moving table TB2 is once delivered to the holder arrangement position P3B by the second deliver means DL2.

Then, this time, the empty holder 50 is delivered to the first moving table TB1 which has been transported to the deliver position p3b by the first deliver means DL1 included in the first moving table TB1. The first moving table TB1 that has received the empty holder 50 is transported up to the deliver position p1 a of the first zone 100 by the inter-zone transport means TR0. Then, the first moving table TB1 is served for the next assembly step.

<Variations>

The embodiment above has described the first assembly step and second assembly step for a case in which the second tip 10b of the sensor element 10 is inserted into the recess 50a of the holder 50, which is not necessarily required. Alternatively, the first tip 10a may be inserted into the recess 50a of the holder 50. In such a case, the members constituting the intermediate assembly product 20 may be annularly mounted in the reverse order of the embodiment above. The intermediate assembly product 20 and tubular body 30 may be fitted together by an appropriate technique.

The first assembly step and second assembly step described in the embodiment above are also applicable to cases other than the assembly of the gas sensor.

As an example, the first assembly step is applicable to a case in which an annularly mounting member, which has a disc or cylindrical shape and has a through hole corresponding to the cross-sectional shape of an elongated member warping within the predetermined dimensional tolerance, is annularly mounted to the elongated member.

The second assembly step is applicable to a case in which a tubular body is annularly mounted to an intermediate assembly product obtained by annularly mounting a plurality of annularly mounting members each having a disc or cylindrical shape to an elongated member that warps within a predetermined dimensional tolerance.

The invention claimed is:

1. A method for assembling a gas sensor, where
   a lower-side held state denotes a state in which a predetermined position on a lower end side of a sensor element is sandwiched by first sandwich means with said lower end being inserted into a recess of a predetermined holder, to thereby hold said sensor element such that at least said lower end extends vertically, said sensor element including ceramic as a main constituent material and having an elongated shape, and
   an upper-side held state denotes a state in which a predetermined position on an upper end side of said sensor element is sandwiched by second sandwich means with said lower end being inserted into said recess, to thereby hold said sensor element such that at least said upper end extends vertically,
   said method comprising:
   a holding step of bringing said sensor element into said upper-side held state;
   a fitting step of fitting a through hole of an annular mounting member with said upper end of said sensor element brought into said upper-side held state, said annular mounting member having a disc shape or cylindrical shape and having said through hole corresponding to a cross-sectional shape of said sensor element; and
   a switching step of switching the held state of said sensor element from said upper-side held state to said lower-side held state after said through hole is fitted with said upper end, to thereby cause said annular mounting member to reach a predetermined annularly mounting position.

2. The method for assembling a gas sensor according to claim 1, wherein
   said holding step, said fitting step, and said switching step are performed on each of a plurality of types of said annular mounting members to obtain an intermediate assembly product.

3. The method for assembling a gas sensor according to claim 2, wherein
   said plurality of types of annular mounting members include:
   ceramic supporters made of ceramic glass; and
   ceramic powder compacts, and
   said ceramic supporters and said powder compacts are annularly mounted alternately.

4. A method for assembling a gas sensor, comprising:
   a first annularly mounting step of obtaining said intermediate assembly product by the method according to claim 2;
   a centering step of sandwiching said intermediate assembly product from its sides by predetermined centering means in a state where said intermediate assembly product is placed on said holder by inserting said lower end into said recess, thereby minimizing an outside diameter of said intermediate assembly product; and a second annularly mounting step of annularly mounting a tubular body to said intermediate assembly product whose outside diameter has been minimized in said centering step.

5. A method for assembling a gas sensor, comprising:

a first annularly mounting step of obtaining said intermediate assembly product by the method according to claim 3;

a centering step of sandwiching said intermediate assembly product from its sides by predetermined centering means in a state where said intermediate assembly product is placed on said holder by inserting said lower end into said recess, thereby minimizing an outside diameter of said intermediate assembly product; and a second annularly mounting step of annularly mounting a tubular body to said intermediate assembly product whose outside diameter has been minimized in said centering step.

6. A gas sensor assembly apparatus, comprising:

a holder having a recess for inserting a sensor element including ceramic as a main constituent material and having an elongated shape;

first sandwich means for sandwiching a predetermined position on a lower end side of said sensor element with said lower end of said sensor element being inserted into the recess of said holder;

second sandwich means for sandwiching a predetermined position on an upper end side of said sensor element with said lower end of said sensor element being inserted into said recess;

an annular mounting member supply portion for supplying an annular mounting member that has a disc shape or cylindrical shape and has a through hole corresponding to a cross-sectional shape of said sensor element; and annular mounting member transport means for transporting said annular mounting member from said annular mounting member supply portion to an annularly mounting process execution position, wherein in a case where a lower-side held state denotes a state in which a predetermined position on said lower end side of said sensor element is sandwiched by said first sandwich means, to thereby hold said sensor element such that at least said lower end extends vertically, and an upper-side held state denotes a state in which a predetermined position on an upper end side of said sensor element is sandwiched by said second sandwich means, to thereby hold said sensor element such that at least said upper end extends vertically, the held state of said sensor element is switched from said upper-side held state to said lower-side held state after said annular mounting member transport means fits said through hole of said annular mounting member with said upper end of said sensor element brought into said upper-side held state, to thereby cause said annular mounting member to reach a predetermined annularly mounting position.

7. The gas sensor assembly apparatus according to claim 6, wherein a plurality of said annular mounting member supply portions and a plurality of said annular mounting member transport means are respectively provided correspondingly to a plurality of types of annular mounting members, and an operation is performed for each of said plurality of types of annular mounting members in order, of fitting said through hole of said annular mounting member with said upper end of said sensor element brought into said upper-side held state, by said annular mounting member transport means, and then switching the held state of said sensor element from said upper-side held state, to said lower-side held state to cause said annular mounting member to reach a predetermined annularly mounting position, thereby obtaining an intermediate assembly product in which said plurality of types of annular mounting members are annularly mounted to said sensor element.

8. The gas sensor assembly apparatus according to claim 7, wherein a plurality of said annularly mounting process execution positions are provided correspondingly to said plurality of types of annular mounting members, said gas sensor assembly apparatus further comprises holder transport means for transporting said holder between said annularly mounting process execution positions, said holder transport means transports, to said annularly mounting process execution positions, said holder holding said sensor element in order, and an operation is performed at each of said annularly mounting process execution positions, of fitting said through hole of said annular mounting member with said upper end of said sensor element brought into said upper-side held state, by said annular mounting member transport means, and then switching the held state of said sensor element from said upper-side held state to said lower-side held state to cause said annular mounting member to reach a predetermined annularly mounting position, thereby obtaining an intermediate assembly product in which said plurality of types of annular mounting members are annularly mounted to said sensor element.

* * * * *